(12) United States Patent
Olsson et al.

(10) Patent No.: US 10,084,945 B1
(45) Date of Patent: *Sep. 25, 2018

(54) CABLE STORAGE DRUM WITH MOVEABLE CCU DOCKING APPARATUS

(71) Applicant: SeeScan, Inc., San Diego, CA (US)

(72) Inventors: Mark S. Olsson, La Jolla, CA (US); James F. Kleyn, Santee, CA (US); Michael E. Turgeon, San Diego, CA (US); Ryan B. Levin, San Diego, CA (US)

(73) Assignee: SEESCAN, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/369,693

(22) Filed: Dec. 5, 2016

Related U.S. Application Data

(63) Continuation of application No. 14/469,536, filed on Aug. 26, 2014, now Pat. No. 9,521,303.

(60) Provisional application No. 61/926,382, filed on Jan. 12, 2014, provisional application No. 61/870,232, filed on Aug. 26, 2013.

(51) Int. Cl.
| | |
|---|---|
| *H04N 5/225* | (2006.01) |
| *H04N 5/232* | (2006.01) |
| *B65H 75/36* | (2006.01) |
| *G01N 21/954* | (2006.01) |

(52) U.S. Cl.
CPC ......... *H04N 5/2253* (2013.01); *B65H 75/364* (2013.01); *G01N 21/954* (2013.01); *H04N 5/23293* (2013.01); *G01N 2021/9542* (2013.01); *G01N 2201/0221* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 2008/0309765 A1 | 12/2008 | Dayan et al. | |
| 2009/0225159 A1 | 9/2009 | Schneider et al. | |
| 2010/0208056 A1 | 8/2010 | Olsson et al. | |
| 2012/0057010 A1 | 3/2012 | Yamauchi | |
| 2012/0147173 A1* | 6/2012 | Lynch | G03B 37/005 348/84 |

FOREIGN PATENT DOCUMENTS

| | | |
|---|---|---|
| DE | 202011004084 U1 | 5/2011 |
| GB | 2380088 A | 3/2003 |

OTHER PUBLICATIONS

International Searching Authority, "Written Opinion of the International Searching Authority" for PCT Patent Application No. PCT/US14/52783, dated Mar. 5, 2015, European Patent Office, Munich.

* cited by examiner

*Primary Examiner* — James M Anderson, II
(74) *Attorney, Agent, or Firm* — Steven C. Tietsworth, Esq.; Heena Sharma

(57) ABSTRACT

Video inspection systems with moveable and dockable CCUs are disclosed. In one embodiment a video inspection system includes a tubular frame element, a camera control unit (CCU), and a docking apparatus mechanically coupled to the frame element so as to allow the CCU to rotate and/or be detached are attached via a user action.

20 Claims, 29 Drawing Sheets

CABLE STORAGE DRUM WITH MOVEABLE CCU DOCKING APPARATUS

CROSS-REFERENCE TO RELATED APPLICATIONS

This application is a continuation of and claims priority to U.S. Utility patent application Ser. No. 14/469,536, entitled CABLE STORAGE DRUM WITH MOVABLE CCU DOCKING APPARATUS, filed Aug. 26, 2014, which claims priority under 35 U.S.C. § 119(e) to U.S. Provisional Patent Application Ser. No. 61/870,232 entitled CABLE STORAGE DRUM WITH MOVABLE CCU DOCKING APPARATUS, filed Aug. 26, 2013, as well as to U.S. Provisional Patent Application Ser. No. 61/926,382, entitled CABLE STORAGE DRUM WITH MOVABLE CCU DOCKING APPARATUS, filed Jan. 12, 2014. The content of each of these applications is hereby incorporated by reference herein in its entirety for all purposes.

FIELD

This disclosure relates generally to cable storage drums used to contain push-cables with inspection cameras and used with video display and/or camera control units (CCUs). More specifically, but not exclusively, this disclosure relates to cable storage drums configured to allow a video display and/or camera control unit to moveably and/or removably dock thereto.

BACKGROUND

Cable storage drums used to contain push-cables with inspection cameras made to interface with a camera control unit (also referred to hereafter as a CCU) for viewing, storing, and/or controlling data and/or video feeds from the inspection camera are known in the art. Many such cable storage drums secure a CCU thereto in a fixed position for use in utility inspection operations. For example, European Patent EP 1,091,159B1, entitled CAVITY INSPECTION DEVICE WITH VIDEO CAMERA, which is incorporated by reference herein, describes an inspection device wherein a monitor for displaying video captured by a video camera is fixed in place with respect to the device frame. These locks or other mechanisms to secure the CCU about a cable storage drum tend to be cumbersome for a user to operate during normal use. Furthermore, existing configurations of cable storage drums with attached CCUs tend to remain fixed in position relative to the frame of the cable storage drum, neglecting a user's need to angle the CCU for ease in viewing during use.

Accordingly, there is a need in the art to address the above-described as well as other problems.

SUMMARY

The present disclosure relates generally to video inspection systems including a frame, camera control unit (CCU) coupled to the frame, cable storage drum coupled to the frame to store a push-cable, and an inspection camera coupled to the push cable, where the inspection system allows the CCU to removably dock to the frame so that the CCU and associated display/monitor remains moveable relative to the frame, such as to allow a user to pivot the CCU and display up or down during use. The CCU may be rotatable relative to the frame and/or attachable to the frame in two or more positions in either of a vertical and/or a horizontal orientation of the system.

Embodiments of a drum and frame with docking apparatus in accordance with aspects of the present disclosure may include a drum element which may further contain a push-cable and inspection camera. The drum element may secure to a frame element configured to remain stationary, while allowing the drum to rotate when dispensing the push-cable into a pipe or other conduit. A docking apparatus may further secure to the frame. The docking apparatus may allow a CCU to dock in a manner allowing the CCU to be moveable in relation to the frame element and/or drum element and/or mountable in two or more orientations, such as oppositely oriented relative to the frame and/or oriented in a vertical or horizontal orientation. The docking apparatus may include one or more docking elements or mechanisms coupled to the frame and/or drum element to detachably receive the CCU. The docking apparatus may include one or more elements on or coupled to the CCU to facilitate removable attachment to the frame and/or drum.

For example, in one aspect, the docking apparatus may include a set of docking elements or mechanisms to allow the user to readily dock and/or undock the CCU with a drum and frame. Such docking elements may allow the CCU to snap into place when docking. The docking element may allow for pre-loading so that the CCU docks with relative ease by being partially engaged, with a contact or snap-action completing engagement. The CCU may further be configured to pivot about the docking mechanisms. Pivoting may be done via a pivoting or rotational axis, and attachment knobs or dials may be rotatable in opposing directions about the release axis to undock the CCU from the frame.

In another aspect, the docking apparatus may automatically reset into a docking ready state upon undocking the CCU, such as through pre-loading. For example, when a user undocks the CCU from a drum and frame, a docking mechanism may reset into a docking ready state such that when the CCU is again docked with the frame via the docking apparatus, the CCU readily snaps back into a docked position.

In another aspect, the CCU may remain oriented in a particular angle or position until a force, generally imparted intentionally by a user, is made to make the CCU pivot or otherwise move. This may be done using a frictional element. A pivot point positioned high upon the docking apparatus, the use of wave springs, conical spring washers, and/or other tensioning or frictional mechanisms may be used to provide the self-supported ability to angle/position the CCU as desired.

In another aspect, the center of gravity of the CCU may be centered at or proximate to a central movable axis of the cable storage drum such that a drum and frame with docking apparatus, which may be positioned in an assortment of different ways during use, may balance so that it will not readily be tipped over during use.

In another aspect, a drum and frame with docking apparatus may be readily carried by a user while the CCU is docked. The CCU may remain docked to the frame via the docking apparatus during transport such that a user need only grasp in one location on the drum and frame with docking apparatus. The CCU may contain multiple handles providing the user options in how best to carry the drum and frame with docking apparatus. The CCU may rotate about a central movable axis during transportation.

In another aspect, the disclosure relates to a video inspection system. The system may include, for example, a frame element. The system may include a camera control unit (CCU). The CCU may include electronics and a display element. The system may include a docking apparatus. The docking apparatus may be mechanically coupled to the frame element and/or the CCU so as to allow the CCU to rotate relative to the frame, about a rotational axis, responsive to a user action. The user action may be a user-applied force. The user-applied force may be a push or pull force applied to the CCU.

Various additional aspects, features, and functionality are further described below in conjunction with the appended Drawings.

BRIEF DESCRIPTION OF THE DRAWINGS

The present application may be more fully appreciated in connection with the following detailed description taken in conjunction with the accompanying drawings, wherein.

DETAILED DESCRIPTION OF EMBODIMENTS

Overview

Figure 1A:
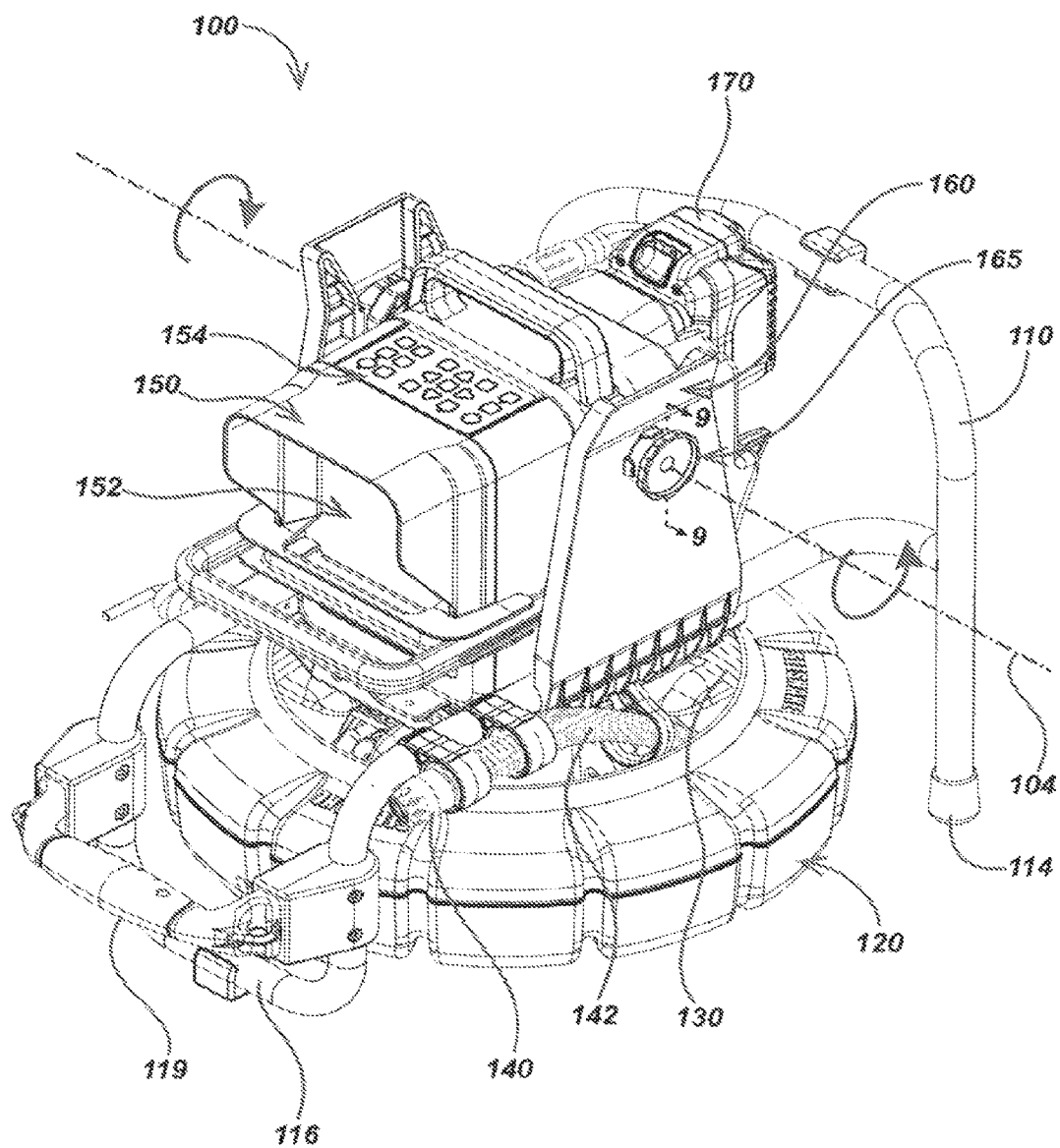
FIG. 1A is an isometric view of an embodiment of a drum and frame with docking apparatus.

The present disclosure relates generally to video inspection systems including a frame, camera control unit (CCU) coupled to the frame, cable storage drum coupled to the frame to store a push-cable, and an inspection camera coupled to the push cable, where the inspection system allows the CCU to removably dock to the frame so that the CCU and associated display/monitor remains moveable relative to the frame, such as to allow a user to pivot the CCU and display up or down during use. The CCU may be rotatable relative to the frame and/or attachable to the frame in two or more positions in either of a vertical and/or a horizontal orientation of the system.

Embodiments of a drum and frame with docking apparatus in accordance with aspects of the present disclosure may include a drum element which may further contain a push-cable and inspection camera. The drum element may secure to a frame element configured to remain stationary, while allowing the drum to rotate when dispensing the push-cable into a pipe or other conduit. A docking apparatus may further secure to the frame. The docking apparatus may allow a CCU to dock in a manner allowing the CCU to be moveable in relation to the frame element and/or drum element and/or mountable in two or more orientations, such as oppositely oriented relative to the frame and/or oriented in a vertical or horizontal orientation. The docking apparatus may include one or more docking elements or mechanisms coupled to the frame and/or drum element to detachably receive the CCU. The docking apparatus may include one or more elements on or coupled to the CCU to facilitate removable attachment to the frame and/or drum.

For example, in one aspect, the docking apparatus may include a set of docking elements or mechanisms to allow the user to readily dock and/or undock the CCU with a drum and frame. Such docking elements may allow the CCU to snap into place when docking. The docking element may allow for pre-loading so that the CCU docs with relative ease by being partially engaged, with a contact or snap-action completing engagement. The CCU may further be configured to pivot about the docking mechanisms. Pivoting may be done via a pivoting or rotational axis, and attachment knobs or dials may be rotatable in opposing directions about the release axis to undock the CCU from the frame.

In another aspect, the docking apparatus may automatically reset into a docking ready state upon undocking the CCU, such as through pre-loading. For example, when a user undocks the CCU from a drum and frame, a docking mechanism may reset into a docking ready state such that when the CCU is again docked with the frame via the docking apparatus, the CCU readily snaps back into a docked position.

In another aspect, the CCU may remain oriented in a particular angle or position until a force, generally imparted intentionally by a user, is made to make the CCU pivot or otherwise move. This may be done using a frictional element. A pivot point positioned high upon the docking apparatus, the use of wave springs, conical spring washers, and/or other tensioning or frictional mechanisms may be used to provide the self-supported ability to angle/position the CCU as desired.

In another aspect, the center of gravity of the CCU may be centered at or proximate to a central movable axis of the cable storage drum such that a drum and frame with docking apparatus, which may be positioned in an assortment of different ways during use, may balance so that it will not readily be tipped over during use.

In another aspect, a drum and frame with docking apparatus may be readily carried by a user while the CCU is docked. The CCU may remain docked to the frame via the docking apparatus during transport such that a user need only grasp in one location on the drum and frame with docking apparatus. The CCU may contain multiple handles providing the user options in how best to carry the drum and frame with docking apparatus. The CCU may rotate about a central movable axis during transportation.

In another aspect, the disclosure relates to a video inspection system. The system may include, for example, a frame element. The system may include a camera control unit (CCU). The CCU may include electronics and a display element. The system may include a docking apparatus. The docking apparatus may be mechanically coupled to the frame element and/or the CCU so as to allow the CCU to rotate relative to the frame, about a rotational axis, responsive to a user action. The user action may be a user-applied force. The user-applied force may be a push or pull force applied to the CCU.

The docking apparatus may, for example, further detachably affix the CCU to the frame. The docking apparatus may detachably fix the CCU to the frame via a latching element or mechanism. The latching element or mechanism may include a pair of knobs rotational about a release axis. The knobs may move away from the frame upon a user release actuation.

The docking apparatus may, for example, include a frictional element for restraining rotation of the CCU. The frictional element may retain the CCU in angled or upright self-supporting position.

The system may, for example, further include a cable storage drum coupled to the frame element. The system may further include a push-cable. The push-cable may be disposed at least partially in an internal volume of the cable storage drum. The system may further include a camera head. The camera head may be mechanically coupled to a distal end of the push-cable, and may be electronically coupled to the CCU. The camera head may be a self-leveling camera head. The system may further include a camera guide and securing mechanism.

The docking apparatus may, for example, include a knob or knobs rotatable on a release axis to release the CCU from attachment to the frame element. The rotational axis and the release axis may be common axes. The knob or knobs may be further movable outward relative to the frame upon a user release actuation. The user release actuation may be a rotation of the knob or knobs about a release axis.

The system may, for example, further include a latch indicator to indicate a state of the docking apparatus. The state may be an open or released state or a closed or locked state. The latch indicator may indicate a state, such as an open or released state, responsive to a user release action of the knob. The user release action may be a rotation of the knob or knobs about the release axis. The indicator may include a visual indicator of a docking apparatus open or released or docking apparatus closed or locked state. The state or states may be indicated by a colored band.

The docking apparatus may be configured to be placed in a docking ready state upon removal of the CCU. The removal of the CCU may be responsive to a user release action. The user release action may be a rotation of a knob or knobs about a release axis.

The center of mass of the frame and drum assembly may, for example, be positioned below the rotational axis.

Various additional aspects, features, and functions are described below in conjunction with FIGS. 1 through 24 of the appended Drawings. In addition to the specific embodiments described subsequently herein, in various alternate embodiments features or elements of the specific embodiments may be combined to implement the same or similar functionality. Accordingly, elements of one embodiment may be combined with elements of other embodiments to implement additional embodiments within the spirit and scope of the present invention.

It is noted that as used herein, the term, "exemplary" means "serving as an example, instance, or illustration." Any aspect, detail, function, implementation, and/or embodiment described herein as "exemplary" is not necessarily to be construed as preferred or advantageous over other aspects and/or embodiments.

The following exemplary embodiments are provided for the purpose of illustrating examples of various aspects, details, and functions of the present disclosure; however, the described embodiments are not intended to be in any way limiting. It will be apparent to one of ordinary skill in the art that various aspects may be implemented in other embodiments within the spirit and scope of the present disclosure.

Example Drums with Moveable CCU Docking Apparatuses

Figure 1B:
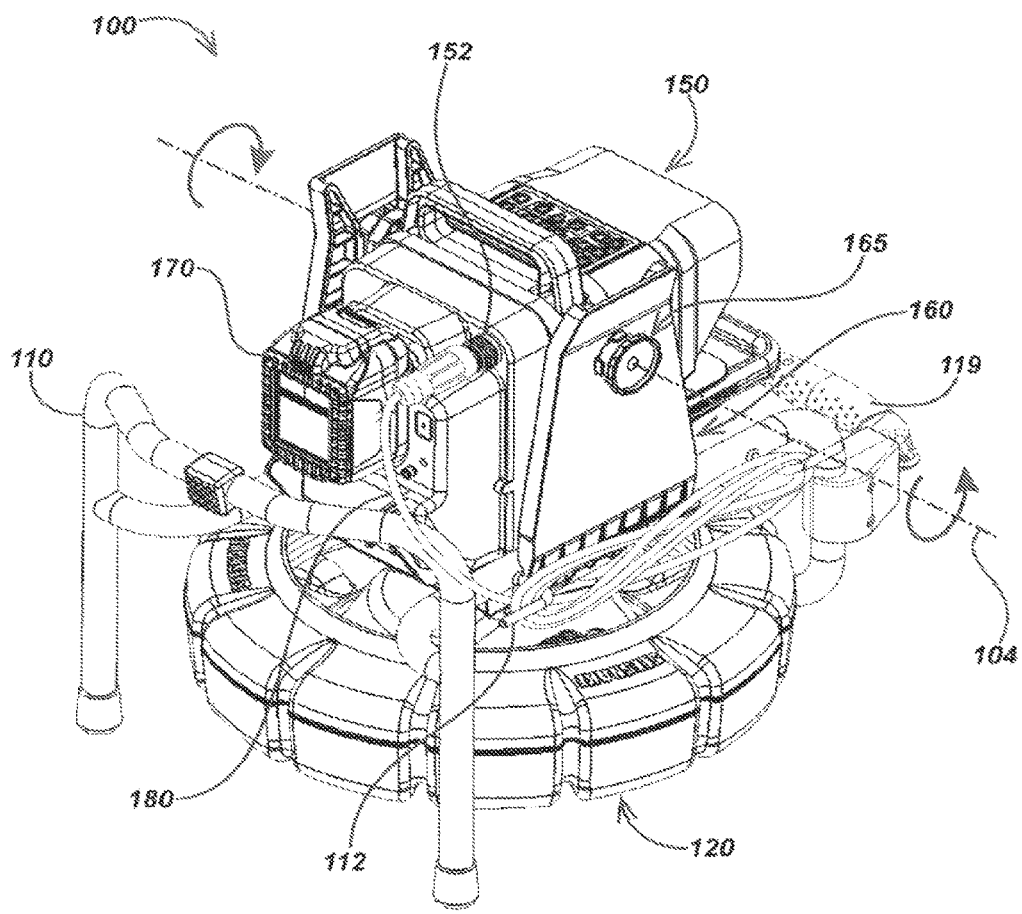
FIG. 1B is a different isometric view of the drum and frame with docking apparatus embodiment of FIG. 1A from a different perspective.
Figure 2:
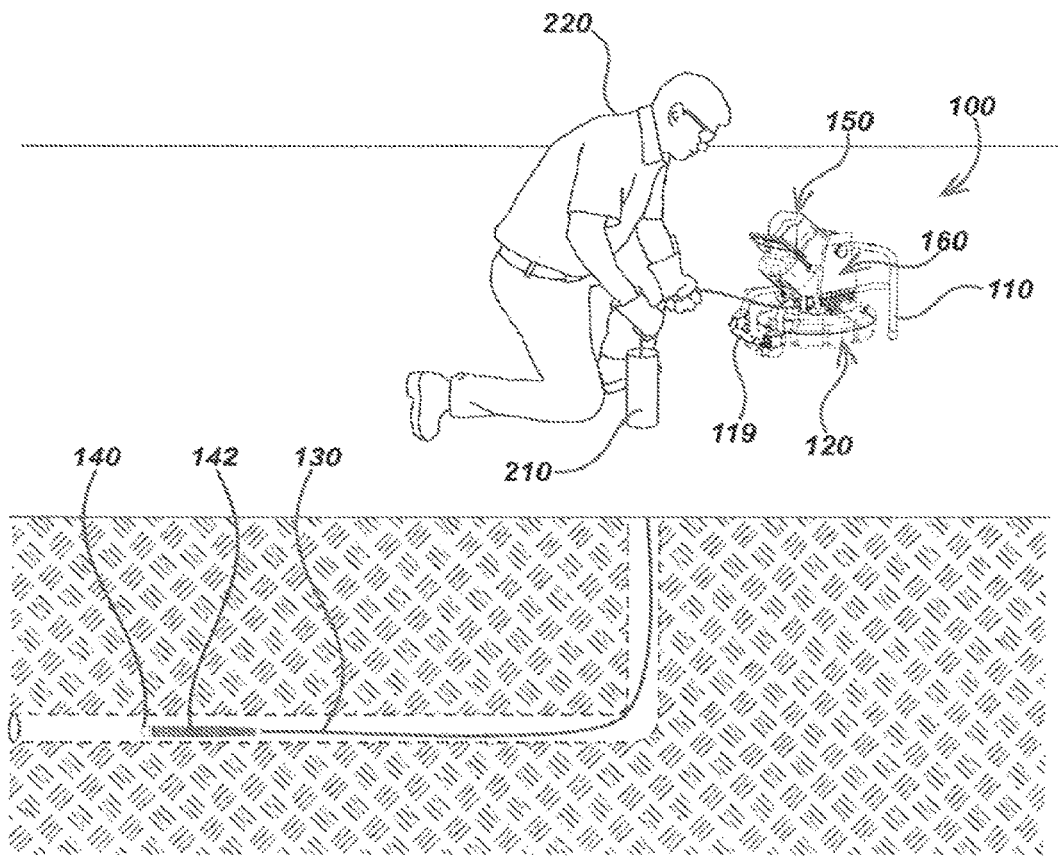
FIG. 2 is an illustration showing a user and the drum and frame with docking apparatus embodiment of FIG. 1A.

Turning to FIGS. 1A, 1B, and 2, an embodiment of a video inspection system 100 including a drum assembly and a docking apparatus, in accordance with aspects of the present disclosure, is illustrated. Inspection system 100 may include a frame, a camera control unit (CCU) with a monitor or display, such as an LCD panel or other display element, a push-cable, a drum for storing the push-cable, an inspection camera coupled to the push-cable, a docking apparatus including a latching element or assembly for coupling and/or rotating the CCU relative to the frame that may include a rotational element with friction retention or other retention mechanisms, and/or other elements as are illustrated in the associated drawings and described herein.

In operation, the CCU and display may be removably coupled to the frame (and/or coupled drum) via a docking apparatus such that they can be moved and/or rotated by an operator to adjust viewing angle or positioning of the display via a user action such as a push or pull on the CCU, and/or may be readily released and reattached, such as by a user action of twisting one or more knobs to put the docking apparatus into a released state, which may be indicated by a latch indicator. The CCU and frame may cooperate with the docking apparatus so that the CCU can be readily removed from the frame using a latch element or assembly or other retaining mechanism configured for rotating the CCU, and/or may be readily attaching or releasing the CCU, such as through a pre-loading element or mechanism, to provide a snap-on attachment action.

Various embodiments of CCUs, frames and drums, and docking apparatus allowing a user to rotate the CCU orientation relative to the frame and/or to allow a user to readily attach and/or release the CCU from the frame may be implemented in accordance with the teachings herein, and the following embodiments are provided as examples. However, other embodiments within the spirit and scope of the present invention may be implemented in combinations of the disclosed details and aspects herein and/or in combinations with similar or equivalent elements that are not explicitly disclosed.

In an exemplary embodiment, as shown in FIG. 1A, frame element 110 is configured to remain stationary upon the ground or other operating surface while suspending a drum element 120 above the operating surface, such as through use of feet, legs, bars, or other ground support elements, in a horizontal orientation. A section 116 of frame 110 may be a tube or bar section horizontally oriented relative to the ground to retain one side of the frame, while another section of the frame may extend to feet 114 as shown. In some uses, the frame may be positioned to stand on end so as to orient the drum element 120 vertically in relation to the ground or operating surface in a vertical orientation (in an exemplary embodiment, an attached CCU may independently be rotated or oriented to a horizontal or vertical orientation, or to an angular orientation in between, irrespective of the orientation of the frame and drum). Other ground support configurations may also be used in alternate embodiments, such as angled orientations, orientations mounted to other devices or systems, vehicle mounting configurations, and the like.

Figure 4:
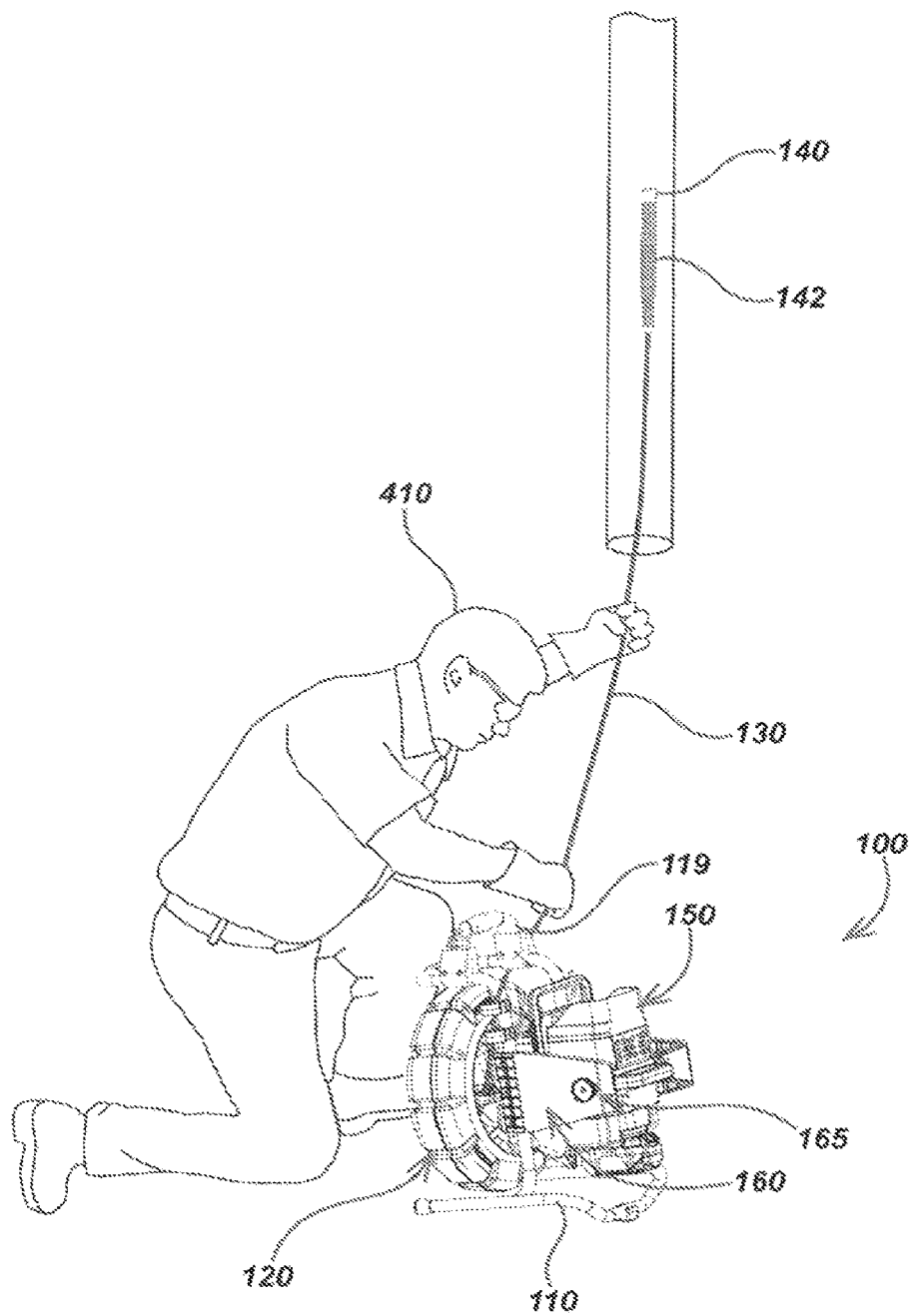
FIG. 4 is an illustration showing a user and the drum and frame with docking apparatus embodiment of FIG. 1A.

In the illustrated configuration, a drum element 120 as coupled to the frame may be held above the ground, in a horizontal orientation (as shown in FIG. 1A) or in a vertical orientation (as shown in FIG. 4). A user may then deploy a camera 140 and spring 142, coupled to a distal end of push-cable 130 which coils within the drum when stored, into a pipe or other conduit to examine the interior of the pipe or conduit. Images or video from the camera 140 may be sent via a conductor element of the push-cable 130 to a proximal end of the push-cable, and then stored in a non-transitory memory of the CCU and/or provided to a user by being rendered on a display of a removably attachable CCU or other electronic computing device or system.

The CCU may be mechanically coupled to the frame via a docking apparatus which may allow the CCU to be rotated or pivoted about a rotational axis (e.g., upon a user action such as pushing or pulling on the CCU), as described subsequently herein, relative to the frame and drum so that a user may select an appropriate viewing angle and/or control access angle to actuate CCU control switches or buttons. In typical embodiments the CCU is readily user-detachable from the frame; however, in some embodiments the CCU may be fixed to the frame so that it may rotate to a desired position upon a user action (e.g., a user pushing or pulling on the CCU as described subsequently herein) and retained in that position (e.g., by friction or other mechanisms as described subsequently herein) but not readily user detachable. In an exemplary embodiment, a pair of knobs of the docking apparatus may be rotated by a user about a release axis to disengage a latching mechanism and allow the CCU to be disconnected from the frame/drum assembly simply by lifting it off. In an exemplary embodiment the release axis is a common axis with the rotational axis; however, in some embodiments, they may be different axes.

In operation, the push-cable may, for example, be deployed into pipe 210 by a user 220 such as shown in FIG. 2, either by hand or mechanically, with images or videos sent back from the inspection camera head 140 to be rendered on display 152 of CCU 150, which may have a display element rotated to a desired angle to allow clear viewing of the images or videos. The user may apply an action to rotate the CCU to change the orientation of the display 152 (e.g., by pushing or pulling on the CCU), and/or may detach the CCU from the frame, via the docking apparatus, for remote operation, transportation, storage, and the like, as described subsequently herein.

The inspection camera 140 may be any of a variety of camera heads for inspection systems as are known or developed in the art. In an exemplary embodiment, the camera head may be a self-leveling camera head; however, various other camera heads may be used in alternate embodiments. Example details of self-leveling camera head embodiments and associated inspection system element embodiments that may be combined with the disclosures herein in various embodiments are described in, for example, co-assigned U.S. patent application Ser. No. 10/858,628, entitled SELF-LEVELING CAMERA HEAD, filed Jun. 1, 2004 and U.S. patent application Ser. No. 13/358,463, entitled SELF-LEVELING INSPECTION SYSTEMS AND METHODS, filed Jan. 25, 2012, the contents of which are incorporated by reference herein.

The drum element 120 may include an interior volume to store the push-cable 130 and inspection camera 140 during transport and/or when not in use, and to receive the push-cable when the inspection camera is withdrawn from the pipe being inspected. During transport, the system 100 may be readily carried by a user gripping various handles located on the CCU 150, various locations on the frame 110, and/or a frame handle 119. The CCU may rotate partially with respect to the frame during transport (in an unlocked state) through the docking apparatus and latching or attachment mechanism, which may allow such rotation in some embodiments through the docking apparatus. In alternate embodiments, a locking element may be used to temporarily lock the CCU relative to the frame during transportation or storage.

System 100 may include a camera control unit (referred hereafter as CCU) 150, which includes electronic circuitry (not shown), a display 152, user inputs and controls 154 for operating the camera head, as well as a processing element and memory (internal to CCU 150, not shown) for storing images and/or other information associated with a video inspection process. The electronics may further include wired or wireless communication modules, such as Bluetooth, WiFi, cellular, and/or other wireless data communication system modules for sending and/or receiving data from external devices or systems. In some embodiments, elements of the docking apparatus may be integral with or coupled to the CCU, whereas in other embodiments the docking apparatus may be entirely or substantially implemented on elements disposed on or coupled to the frame and/or drum.

The system may include a docking apparatus including a docking element with a latching element or mechanism or assembly and/or a rotational element or mechanism or assembly to removably dock the CCU 150 to the frame 110, such as with a docking element 160, as well as to allow the CCU 150 to rotate relative to the frame and drum when attached. Various latching and rotational elements may be used in different embodiments. In an exemplary embodiment the latching and rotational elements as described herein may be used, however, these are not intended to be limiting.

In operation in the illustrated embodiment, docking element 160 allows the CCU 150 to rotate or pivot relative to the frame 110, such as about pivoting or rotational axis 104 as shown in FIG. 1A, to allow a user to adjust the viewing angle during video inspections or other operations. Docking lock and release actions may be implemented via knobs or other rotational elements about a corresponding release axis as described subsequently herein. The rotational and/or release axes may be positioned above the center of mass of the drum and frame assembly when the system is in a selected position, such as when the system is in a horizontal orientation as shown in FIG. 1A on the ground, so as to improve stability (e.g. the center of gravity is kept below the docking/pivoting axis to maintain stability against falling over). The CCU may be attachable to the frame, such as through docking element 160 of the docking apparatus, in one of two opposite orientations, so that a user may attach the CCU with the display facing either side of the frame/drum, depending on a user-desired orientation. The docking apparatus may be configured to place a locking mechanism into a docking ready state subsequent to CCU release to facilitate snap-action locking when the CCU is subsequently pushed back onto the frame assembly and docking apparatus.

Examples of various details of embodiments of CCUs and associated elements that may be used in conjunction with the disclosures herein in various embodiments are described in, for example, co-assigned U.S. patent application Ser. No. 13/346,668, entitled PORTABLE CAMERA CONTROLLER PLATFORM FOR USE WITH PIPE INSPECTION SYSTEM, filed Jan. 9, 2012, U.S. patent application Ser. No. 13/774,351, entitled DOCKABLE TRIPODAL CAMERA CONTROL UNIT, filed Feb. 22, 2013, U.S. patent application Ser. No. 13/941,381, entitled SELF-GROUNDING PORTABLE CAMERA CONTROL UNIT FOR USE WITH PIPE INSPECTION SYSTEM, filed Jul. 12, 2013, and U.S. patent application Ser. No. 14/216,358, entitled SMART CABLE STORAGE DRUM AND NETWORK NODE SYSTEMS & METHODS, filed Mar. 17, 2014.

The docking element 160 of the docking apparatus may removably couple the CCU to the frame and/or may allow rotation about a rotational axis through or adjacent to the frame assembly. For example, in an exemplary embodiment, the docking element may include a docking snap and release mechanism 165 (as well as other elements as illustrated and described herein) to allow a user to undock the CCU 150 from the frame 110 via a simple push action. The CCU may be releasable via one or two rotatable knobs or other elements of the docking apparatus to allow a user to readily release the CCU from the frame, such as through a user action of rotation of the knobs (e.g., knob element 740 as shown in FIG. 7) in one or two rotational directions about a release axis (a user release actuation of the knob). The knobs may rotate about a release axis defined by rotation of the knobs and/or may move outward from the frame responsive to the release actuation, such as through threading or ramp features on the knobs and/or coupled elements. A latch indicator for indicating docking apparatus state (i.e., open or released, or closed), such as described in conjunction with FIGS. 20 and 23A and 23B, may be included to indicate the state of the docking apparatus. The CCU 150 may pivot or move about a pivot or rotational axis 104, which may be implemented via an element or elements of the docking apparatus affixed to the frame and/or to an element or elements of the docking apparatus affixed to the CCU in alternate embodiments, or in elements affixed to both the frame and the CCU. The release axis may be a common axis with the rotational or pivoting axis.

The pivot or rotational axis may be located at various positions above the drum 120 in various embodiments. In an exemplary embodiment, the pivot axis 104 may be formed centrally between docking snap and release mechanisms 165 on either side of the CCU 150, and may be rotatable knobs or other mechanisms to allow rotation, as well as retention via spring action or friction. Locating of the rotational axis above the center of gravity of the drum/frame assembly may aid in maintaining stability of the system during use. The rotatable knobs may include threading or other features to allow the knobs to rotate about a release axis and/or to move in or out relative to the frame. The latch indicator or docking apparatus state may be provided in conjunction with the knobs, such as by providing a colored indicator when the knobs move away from the frame as described subsequently herein with respect to FIG. 20 and FIG. 23A and FIG. 23B. The release axis may be a common axis with the pivoting or rotational axes. Other release and/or pivot or rotation mechanisms may be used in alternate embodiments.

In operation, the CCU 150 may pivot or rotate about axis 104 relative to the frame 110 to allow a user to adjust viewing angle or protect the display from sunlight, water, or other environmental conditions. The knobs may be rotated about the release axis to place the docking apparatus in a released state position so that the CCU may be readily lifted from the frame/drum assembly for detached use, transportation, or storage. In an exemplary embodiment, the pivot or rotational axis and the release axis are common axes so that the CCU rotates about an axis that is common to the rotational axis of the knobs that are rotated to release the CCU from the frame.

The CCU 150 may connect to a power source such as a battery 170 to supply operating power. The battery 170 may be a standard rechargeable battery or, in some embodiments, may be an intelligent or "Lucid" battery such as is described in, for example, co-assigned U.S. patent application Ser. No. 13/252,721, entitled MODULAR BATTERY APPARATUS, SYSTEMS, AND METHODS, filed in Jun. 25, 2012, the content of which is incorporated by reference herein.

As illustrated in FIG. 1B, a cord or cable 180 may connect to the CCU 150 and drum element 120 for purposes of providing power and/or establishing a data communication link between the CCU and the camera head. The data communication link may further be established with other connected devices and/or sensors and/or other external devices or systems, such as a remote computing system or a buried utility locator, cellular phone, tablet, or other device or system. For example, in some embodiments, there may be a counting device configured to determine and measure rotations of the drum for purposes of deriving, for instance, the quantity of push-cable dispensed and/or distance an inspection camera may have traveled from the drum. Such a counting device may be, for example, a cable counting device as disclosed in co-assigned U.S. patent application Ser. No. 12/766,742, entitled PIPE INSPECTION CABLE COUNTER AND OVERLAY MANAGEMENT SYSTEM, filed Apr. 23, 2010, the content of which is incorporated by reference herein.

In use, the data communication link may be utilized to update counter calibration data and/or other data or information, such as sensed environmental data, camera video or images, location/position information (e.g., as determined with a GPS or other location-determination device), and the like. The data communication link may be implemented via a wired communication link or, in some embodiments, via a wireless communication link, such as through use of a Bluetooth, WiFi, Cellular, or other data communications channel via associated communication modules. The CCU 150 may have a cord terminal 152 for connecting the cord 180. The cord 180 may further connect to a hub (not illustrated) centrally on the drum element 120. A cord retainer fixture 112 formed on the frame element 110 may be used for storing excess amounts of the cord 180 and/or the cord 180 when not connected to a CCU such as the CCU 150.

Various aspects and details of embodiments of cable storage drums, CCUs, inspection cameras, and push-cables as may be combined in various embodiments with the disclosures herein are described in co-assigned U.S. patent application Ser. No. 13/787,711, entitled DUAL SENSED LOCATING SYSTEMS AND METHODS, filed on Mar. 6, 2013, U.S. patent application Ser. No. 13/346,668, entitled PORTABLE CAMERA CONTROLLER PLATFORM FOR USE WITH PIPE INSPECTION SYSTEM, filed on Jan. 9, 2012, U.S. patent application Ser. No. 13/774,351, entitled DOCKABLE TRIPODAL CAMERA CONTROL UNIT, filed on 22 Feb. 2013, U.S. patent application Ser. No. 12/704,808, entitled PIPE INSPECTION SYSTEM WITH REPLACEABLE CABLE STORAGE DRUM, filed Feb. 12, 2010, U.S. patent application Ser. No. 12/371,540, entitled PUSH-CABLES FOR PIPE INSPECTION SYSTEM, filed Feb. 13, 2009, U.S. patent application Ser. No. 13/073,919, entitled PIPE INSPECTION SYSTEM WITH JETTER PUSH-CABLE, filed Mar. 28, 2011, U.S. patent application Ser. No. 13/214,208, entitled ASYMMETRIC DRAG FORCE BEARINGS FOR USE WITH PUSH-CABLE STORAGE DRUMS, filed Aug. 21, 2011, U.S. patent application Ser. No. 12/704,808, entitled PIPE INSPECTION SYSTEM WITH REPLACEABLE CABLE STORAGE DRUM, filed Feb. 12, 2010, U.S. Pat. No. 6,545,704, U.S. Pat. No. 5,939,679, U.S. Pat. No. 6,831,679, U.S. Pat. No. 6,958,767, and U.S. Pat. No. 6,862,945. These patents and patent applications may be collectively referred to herein as the "incorporated applications." The content of each of these patents and patent applications is incorporated by reference herein in its entirety.

Figure 3:
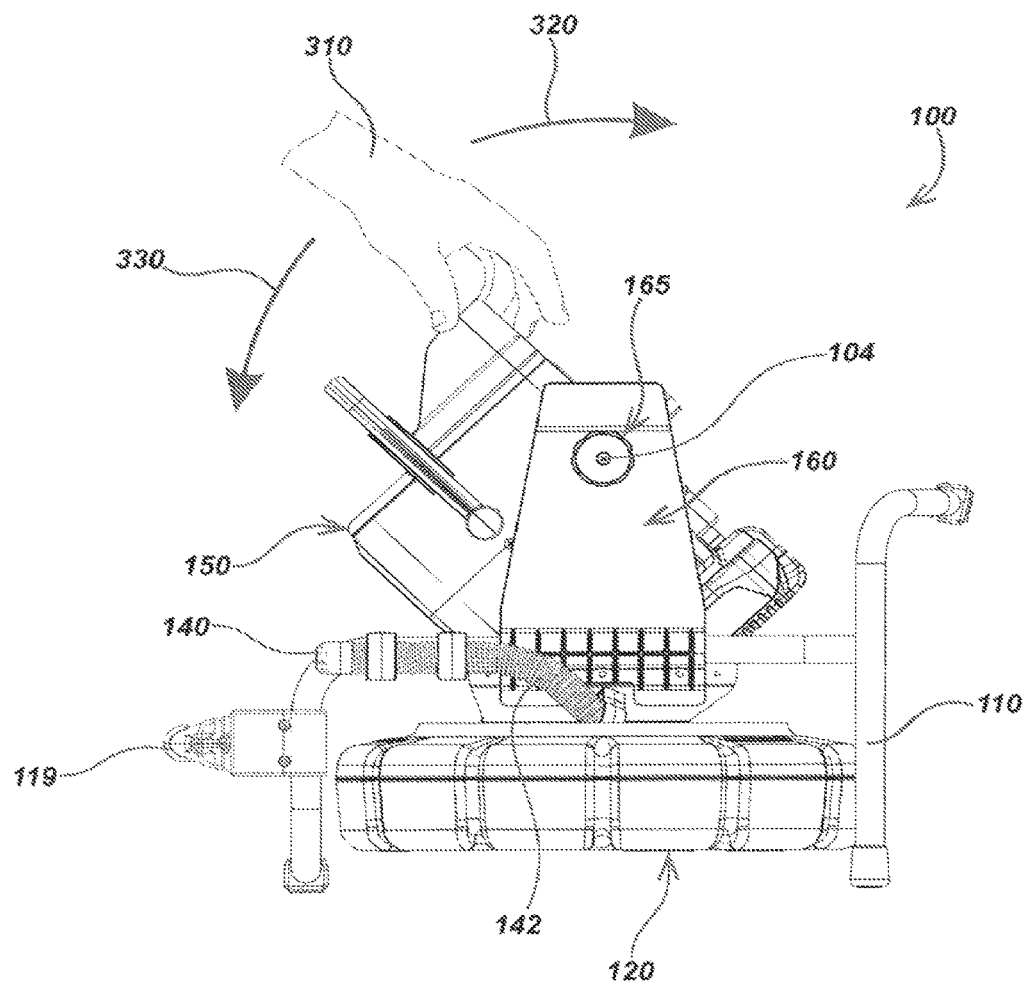
FIG. 3 is a side view of the drum and frame with docking apparatus embodiment of FIG. 1A.

Turning to FIGS. 3 and 4, the CCU 150, when docked onto the docking element 160 of the docking apparatus, may rotate about a pivoting or rotational axis in relation to the frame element 110 and drum element 120 so as to provide swivel or pivoting movements, such as about axis 104 or other about other rotational elements, such as axles, pins, bearings, gears, and the like, relative to the frame and drum. For example, as illustrated in FIG. 3, a user 310 may impart force onto the CCU 150 causing the CCU 150 to rotate or pivot in a direction 320 or 330, such as about rotational axis 104. The CCU orientation may be maintained by frictional force until a sufficient force is applied to overcome the friction and allow the CCU to move relative to the frame. The frictional force may be fixed in some embodiments or, in alternate embodiments, may be variable or user-adjustable. Knobs as described subsequently herein, may rotate about a release axis (i.e., to allow release of the CCU by turning the knobs through full or partial rotations in a clockwise or counterclockwise direction to release a latching action retaining the CCU). The release axis and the rotation axis may be common axes in an exemplary embodiment.

For example, the CCU 150 and docking element 160 may remain oriented in a particular angle or position, such as through the use of a frictional contact or other retaining mechanism, until a sufficient force, such as a force imparted along directions 320 or 330 by the user 310 sufficient to overcome the restraining frictional force, makes the CCU pivot or otherwise move or rotate about pivot axis 104 (FIG. 3).

The rotational or pivot point or axis, such as the pivot axis 104 (FIG. 3), by which the CCU 150 may be rotated by a user action relative to the frame and drum, may be positioned relatively high upon the docking element 160 (located about the docking snap and release mechanisms 165) and CCU 150 such that a user may angle/orient the CCU 150 in a particular position and have it remain in that particular orientation until it is moved to a new position by a user through application of a sufficient user action/force to overcome the frictional retaining force holding the CCU in place.

For example, as shown in FIG. 4, the user 410 may orient the CCU 150 in a vertical position to make the display of the CCU 150 accessible to a user during an inspection operation and in the same relative orientation. The CCU 150 may remain self-supported in the vertical orientation without the user 410 supporting it upright (e.g. by holding the CCU or frame in place by hand), thereby freeing the user 410 to efficiently and continually monitor the pipe inspection. Other frictional elements, gears, ratcheting elements, and the like may also be used to retain the CCU 150 in the user-selected orientation in various embodiments until the user performs a further action to move or release the CCU from the selected orientation. If the user moves the position up or down, such as by providing a new force (e.g., a push or pull) to the CCU, the CCU may be readily readjusted for optimal viewing in the user's new position, and may again be retained in the new position until a subsequent user action is applied.

Tension to allow the CCU 150 the self-supported ability to be angled or positioned may be provided, at least in part, by establishing a high pivot point, such as at a pivot point established about the docking snap and release mechanisms 165 as shown. Wave springs, conical spring washers, ratcheting elements or gears, pins, and/or other frictional or tensioning mechanisms may further be used to provide the self-supported ability to angle/position the CCU 150 as desired. In an exemplary embodiment the center of gravity of the CCU 150 may be substantially centered about the central axis of the drum element 120 in the various orientations of inspection system 100 to further balance and prevent the inspection system 100 from readily being tipped over during use, such as through being accidentally bumped or pushed.

Figure 5:
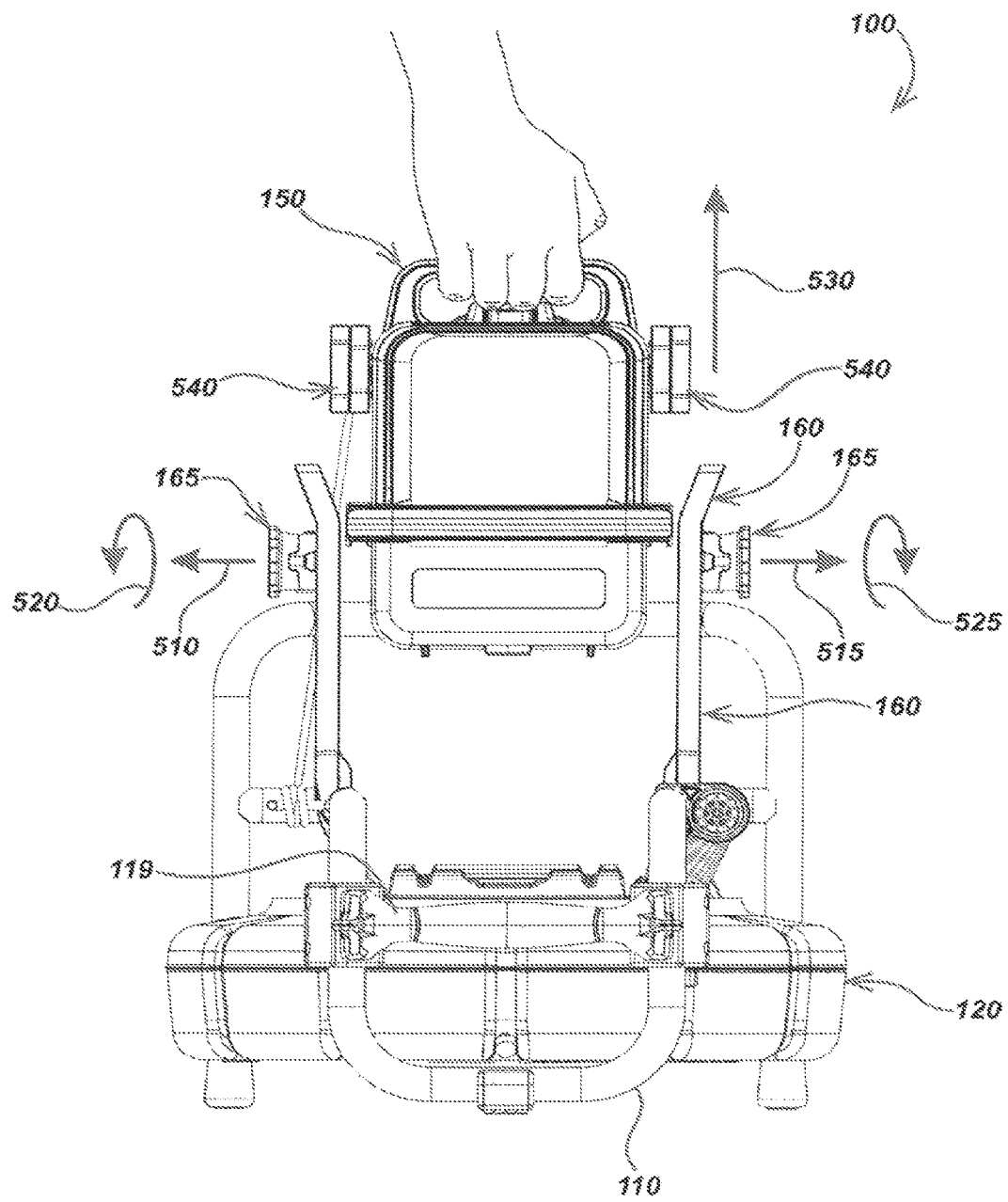
FIG. 5 is a front view of the drum and frame with docking apparatus embodiment of FIG. 1A.

Turning to FIG. 5, details of an exemplary embodiment of a latch release mechanism of the docking apparatus allowing a user to quickly remove the CCU from the frame are illustrated. In the illustrated embodiment, a user may interact with docking snap and release mechanism 165 to release the CCU from the docked or closed position by rotating knobs (e.g., knob element 740 as shown in FIG. 7) on opposite sides of the frame in one direction or, in some embodiments, in either of two directions (i.e. clockwise or counterclockwise) to release the attachment of CCU to the frame so that a user can lift the CCU off the frame for storage, transport, re-attachment in a new orientation, and the like. Once released, the docking snap and release mechanism may be pre-loaded to a docking ready state so as to allow quick reattachment of the CCU (e.g., by having a user merely push the CCU back onto the docking apparatus elements coupled to the frame to have the CCU fixedly snap into place).

In the illustrated embodiment, upon pulling knobs (e.g., knob element 740 as shown in FIG. 7) or handles in outwards directions 510 and 515, a rotational force in direction 520 and 525 may be applied by the user along a release axis to each respective docking snap and release mechanism 165, thereby allowing the CCU 150 to be unlocked/undocked and be pulled away from the docking element 160 in an upwards direction 530. During rotation about the release axis, the knobs or handles of element 165 may move, via threading or other mechanisms, outward from the frame, and may stay in the rotated position until the CCU is lifted away from the frame, after which they may snap back when the CCU is reattached so as to put the docking apparatus in a docking ready state.

The docking snap and release mechanism 165 of the docking apparatus may reset into a docking ready state upon undocking the CCU 150 such that when the CCU 150 is again docked with the docking element 160, the CCU 150 readily snaps back into a docked state (for example, by having the knobs rotate about the release axis to return to their original non-rotated position and inward towards the frame). When docked again, a series of guide features formed on the inward facing sections on the docking element 160 may guide a pivotal docking mechanism 540 attached to either side of the CCU 150 into place. Various details of the exemplary embodiment of the docking snap and release mechanism 165 of the docking apparatus and the docking and pivot mechanism 540 of the docking apparatus are described in greater detail subsequently herein.

Figure 6:
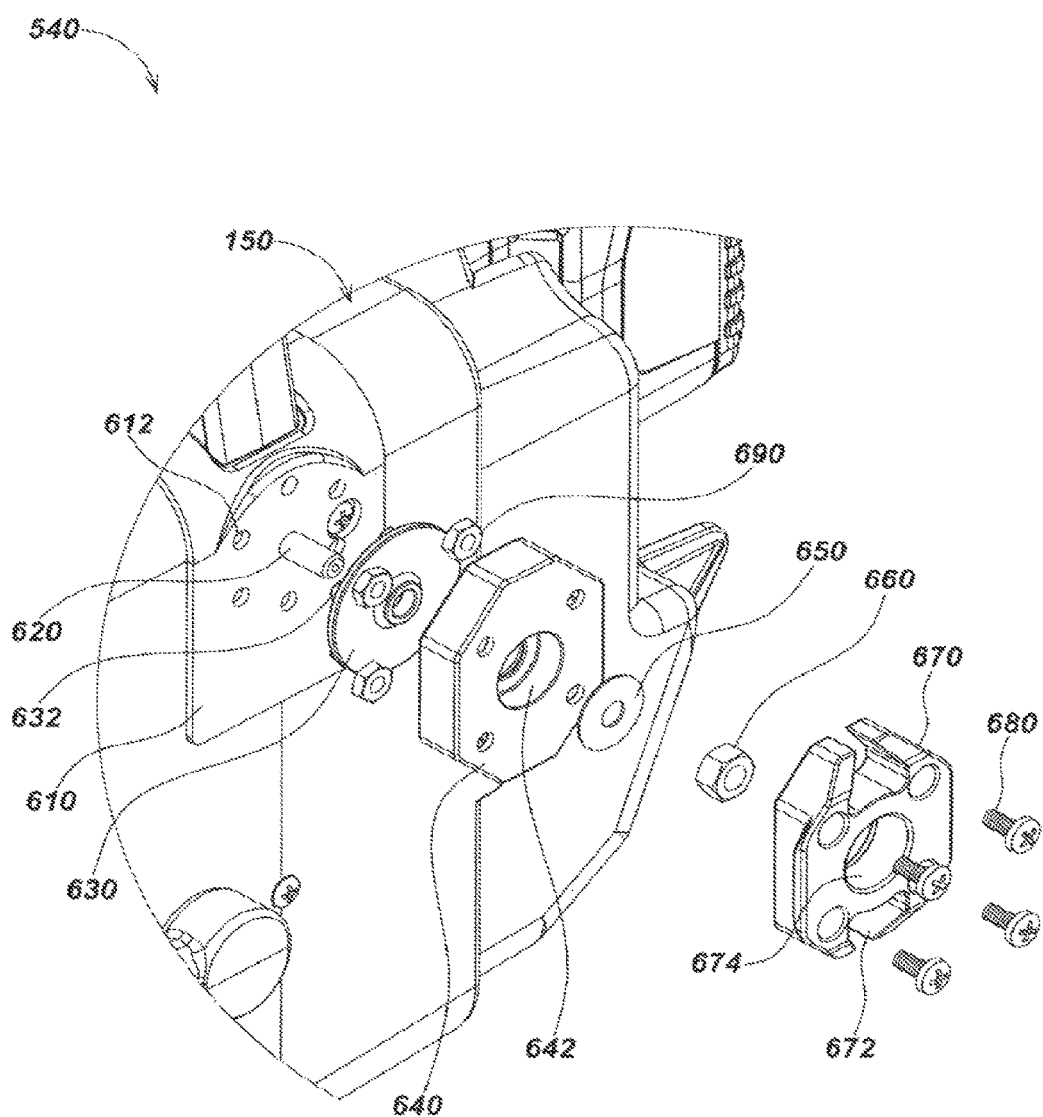
FIG. 6 is an exploded view of a pivotal docking mechanism embodiment.

Turning to FIG. 6, additional details of an embodiment of a docking apparatus and associated CCU are illustrated. As shown in FIG. 6, each docking and pivot mechanism 540 may secure to a CCU saddle mounting element 610, which may be an element of the docking apparatus affixed to the CCU or may be integral with the CCU. The CCU saddle mounting element 610 may secure to the CCU 150 via high strength bonding tape, adhesives, screws, straps, and/or other mechanisms to fix the CCU saddle mount element 610 in place. The CCU saddle mount element 610 may be formed with a series of divots 612 and secure a threaded mounting post 620 centrally within a circle formed by the divots 612. An inner plate 630 formed with a series of inward facing inner plate nubbins 632 (partially obscured) may be seated about the threaded mounting post 620 in assembly such that each inner plate nubbin 632 may seat within one of the divots 612 on the CCU saddle mount element 610 and hold the inner plate 630 stationary thereto against rotational forces.

An inner pivot element 640 may further sit atop the inner plate 630 about the threaded mounting post 620. The inner pivot element 640 may be formed with a central cavity 642 into which a disk spring 650 may be seated. A nut 660 may secure to the threaded mounting post 620 after the disk spring 650 securing the disk spring 650, inner pivot element 640, and inner plate element 630 to the threaded mounting post 620 secure to the CCU saddle mounting element 610 and CCU 150.

The inner pivot element 640 may rotate about the threaded mounting post 620. The disk spring 650, which may be a wave spring or conical spring washer, may provide tension to the inner pivot element 640. A docking plate 670 may secure to the inner pivot element 640 via bolts 680 retained by nuts 690 seated behind the inner pivot element 640. The docking plate 670 may be formed to include a reset gap feature 672 which may guide components on the docking snap and release mechanism 165 to automatically reset into a docking ready state upon undocking the CCU 150. The reset gap feature 672 may be shaped with a small central opening below a larger void.

Figure 7A:
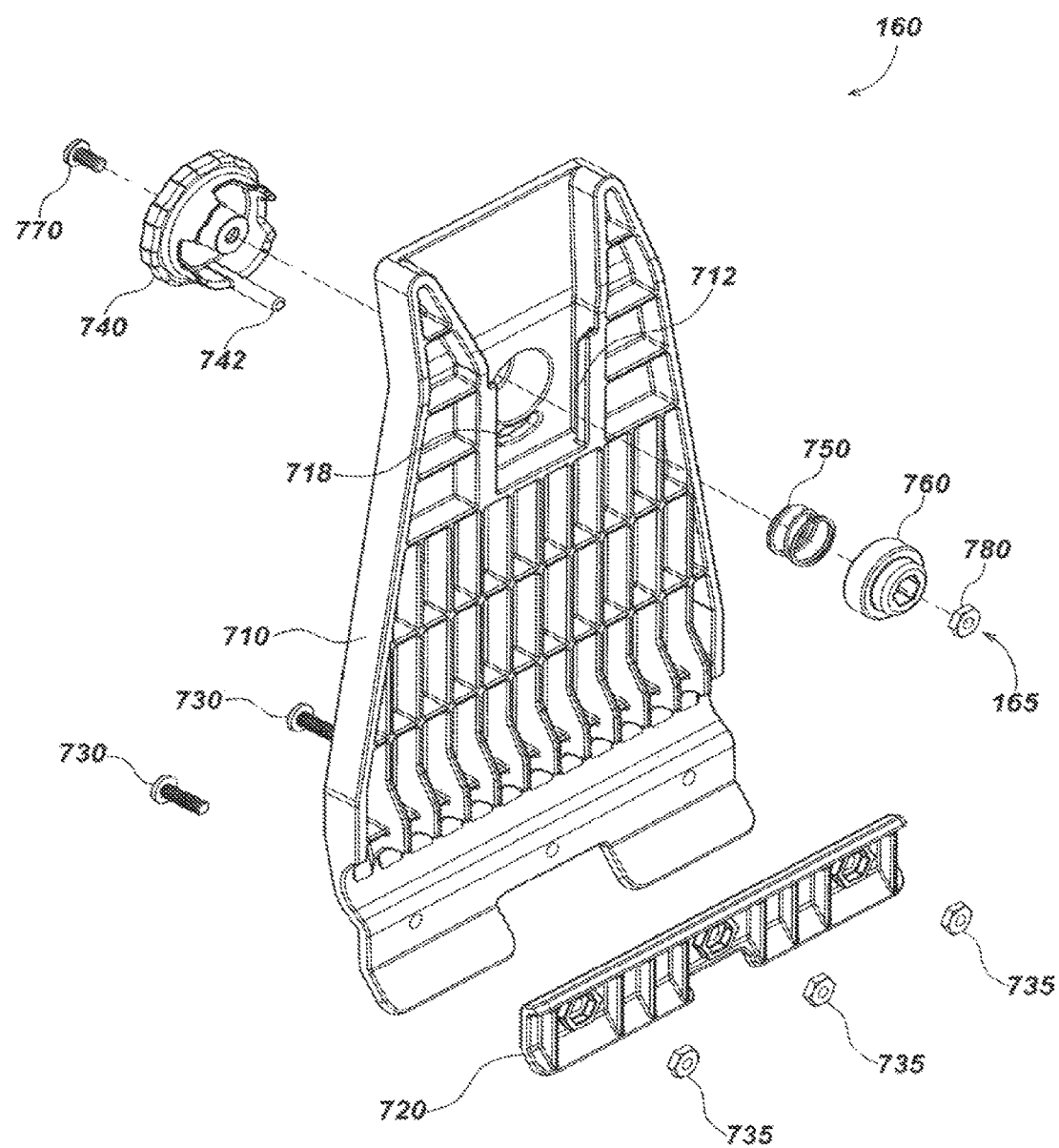
FIG. 7A is an exploded view of details of a docking apparatus embodiment.
Figure 7B:
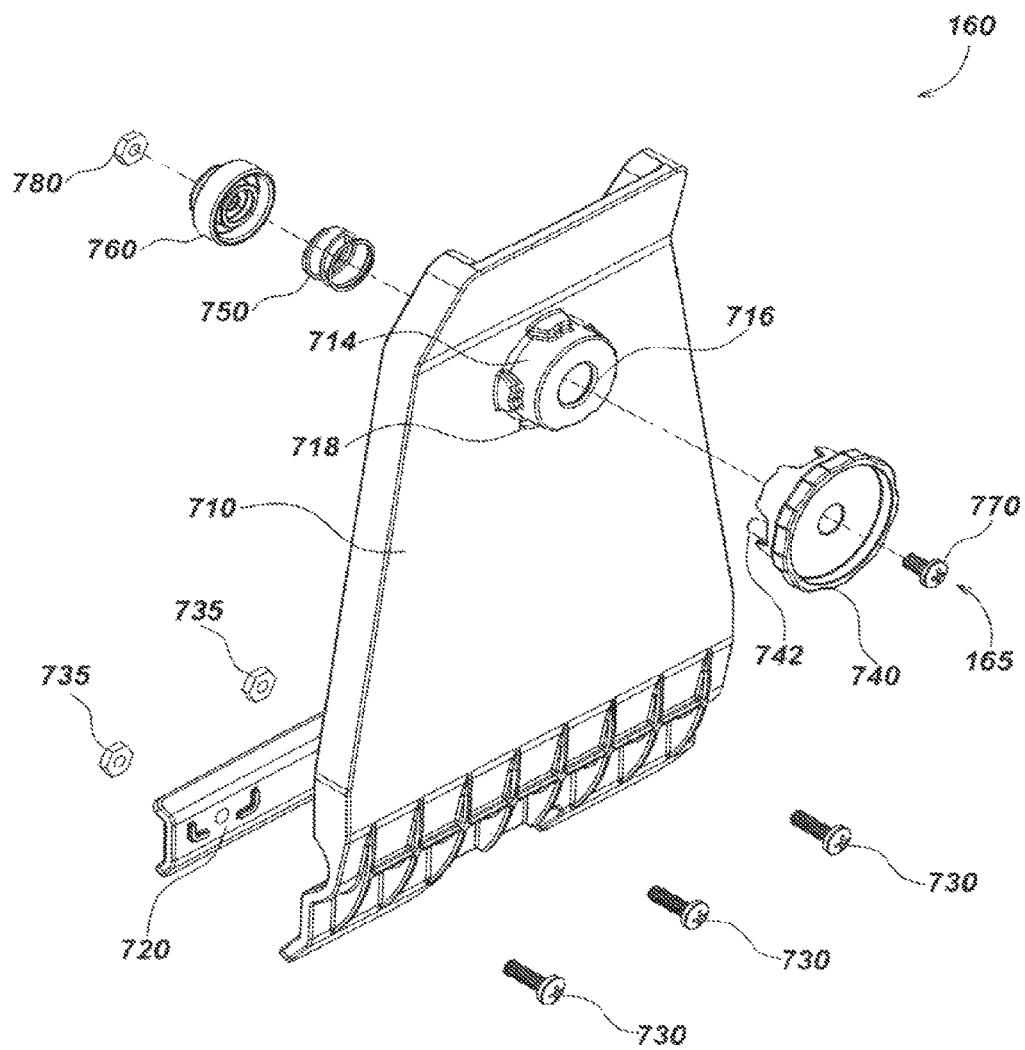
FIG. 7B is an exploded view of the docking apparatus embodiment of FIG. 7A from a different perspective.

FIG. 7A and FIG. 7B illustrate additional details of a docking apparatus embodiment illustrating elements of the docking apparatus coupled to or integral with the frame to which the CCU is attached. As shown in FIG. 7 and with respect to FIG. 1A and FIG. 6, inward sloping sides around the larger void may guide a docking reset prong 742 (FIG. 7A) on the docking snap and release mechanism 165 towards the small central opening and actuate the resetting into the docking ready state when the CCU 150 is undocked. When in a docked state, a docking cavity 674 formed centrally on the docking plate may accommodate the end of a spring retaining docking snap element 760 (FIG. 7A) on the docking snap and release mechanism 165 (FIG. 1A) and dock the CCU 150 to the docking element 160 (FIG. 1). Additional detail regarding various docking component embodiments as well as the automatic resetting of the device into a docking ready state and other docking functions are described subsequently herein.

As shown in FIG. 7A and FIG. 7B, the docking element 160 with attached docking snap and release mechanism 165 may further be comprised of a set of docking bracket arms 710 and bottom bracket element 720 that attach to the frame element 110 (FIG. 1) via bolts 730 and nuts 735 or via other attachment mechanisms. The inward facing side of each docking bracket arm 710, as illustrated in FIG. 7A, may be formed with a guide feature 712 for guiding corresponding pivotal docking mechanisms 540 (FIG. 5) and attached CCU 150 (FIG. 1) during docking and undocking of the CCU 150 (FIG. 1).

As illustrated in FIG. 7B, the outward facing side of each docking bracket arm 710 may be formed with a release nubbin 714 and hole feature 716 about which the various components of the docking snap and release mechanism 165 may be seated in assembly. A knob element 740 of the docking snap and release mechanism 165 may seat onto the release nubbin 714, while a spring 750 seated into a spring retaining docking snap element 760 may sit partially protruding from within the cavity formed along the inward facing side of each docking bracket arm 710 by the release nubbin 714.

A bolt 770 may feed centrally through the knob element 740, the hole feature 716 formed centrally through the release nubbin 714, the spring 750 seated onto the spring retaining docking snap element 760, and secure via nut 780 which may further seat within the back of the spring retaining docking snap element 760 in assembly. When assembled, a docking reset prong 742 formed pointing inwards along the circumference on each knob element 740 may fit into and be provided space to move back and forth within a groove 718 formed through each docking bracket arm 710. The spring 750 may create tension such that a user may be able to pull the knob element 740 outward and rotate about the release axis. When the knob element 740 is pulled outward, the spring retaining docking snap element 760 may also be made to move outward and seat further within the cavity formed along the inward facing side of each docking bracket arm 710 by the release nubbin 714.

Figure 8A:
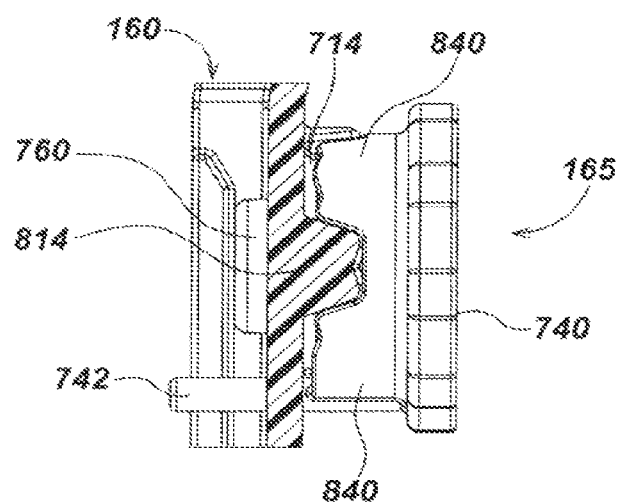
FIG. 8A is a side view illustrating details of a docking snap and release mechanism embodiment in a docking ready state.
Figure 8B:
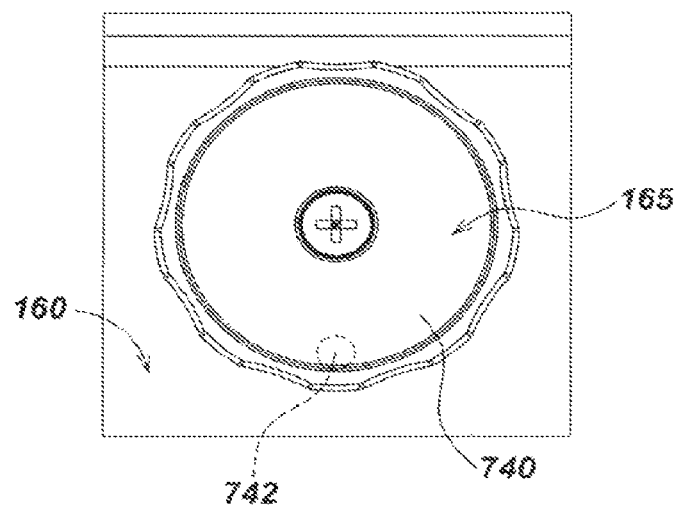
FIG. 8B is a front view illustrating additional details of the docking snap and release mechanism embodiment of FIG. 8A in a docking ready state.

As illustrated in FIGS. 8A and 8B, when in a docking ready state, series release nubbin keying teeth 814 formed on the release nubbin 714 may key between a series of knob keying teeth 840 formed onto the knob element 740. The docking reset prong 742 may be positioned centrally such that when the CCU 150 (FIG. 1) is docked, the docking reset prong 742 may align to the opening on the reset gap feature 672 (FIG. 6).

Figure 8C:
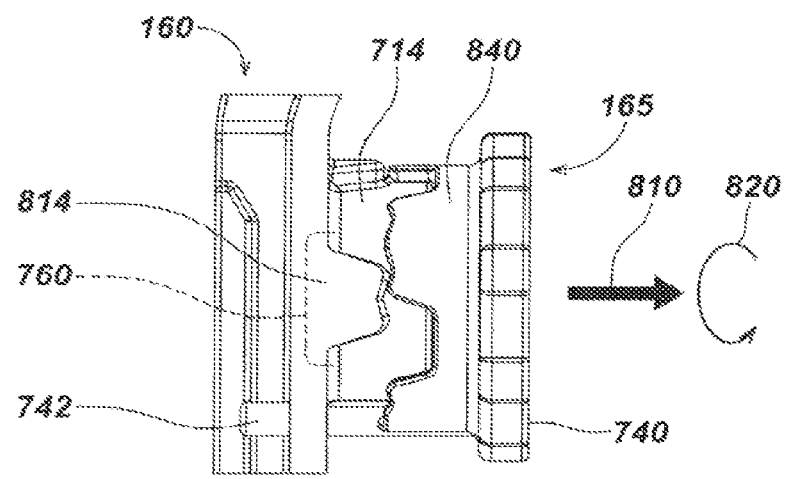
FIG. 8C is a side view illustrating details of a docking snap and release mechanism embodiment when moved out of the docking ready state.
Figure 8D:
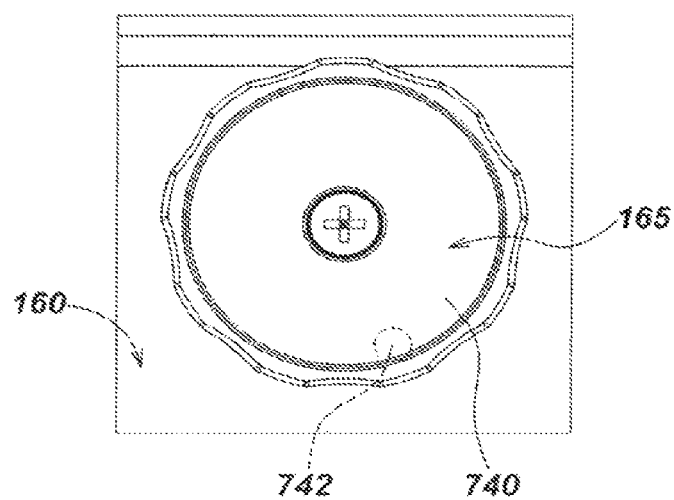
FIG. 8D is a front view illustrating additional details of the docking snap and release mechanism embodiment of FIG. 8C when moved out of the docking ready state.

Turning to FIGS. 8C and 8D, when the knob element 740 is pulled in an outward direction 810 and rotated in a direction 820, the knob keying teeth 840 formed onto the knob element 740 may rest upon the release nubbin keying teeth 814 formed on the release nubbin 714. In such a state, the docking reset prong 742 on the knob element 740 may move within the reset gap feature 672 (FIG. 6) such that the docking reset prong 742 no longer aligns with the opening on the reset gap feature 672 (FIG. 6). When the CCU 150 (FIG. 1) is undocked, the docking reset prong 742 may be forced to slide along the sides of the reset gap feature 672 (FIG. 6) until the docking reset prong 742 aligns with the opening on the reset gap feature 672 (FIG. 6), thus automatically resetting into a docking ready state upon undocking the CCU 150, allowing the CCU to readily snap onto the frame and be set in a locked docked state.

Figure 9:
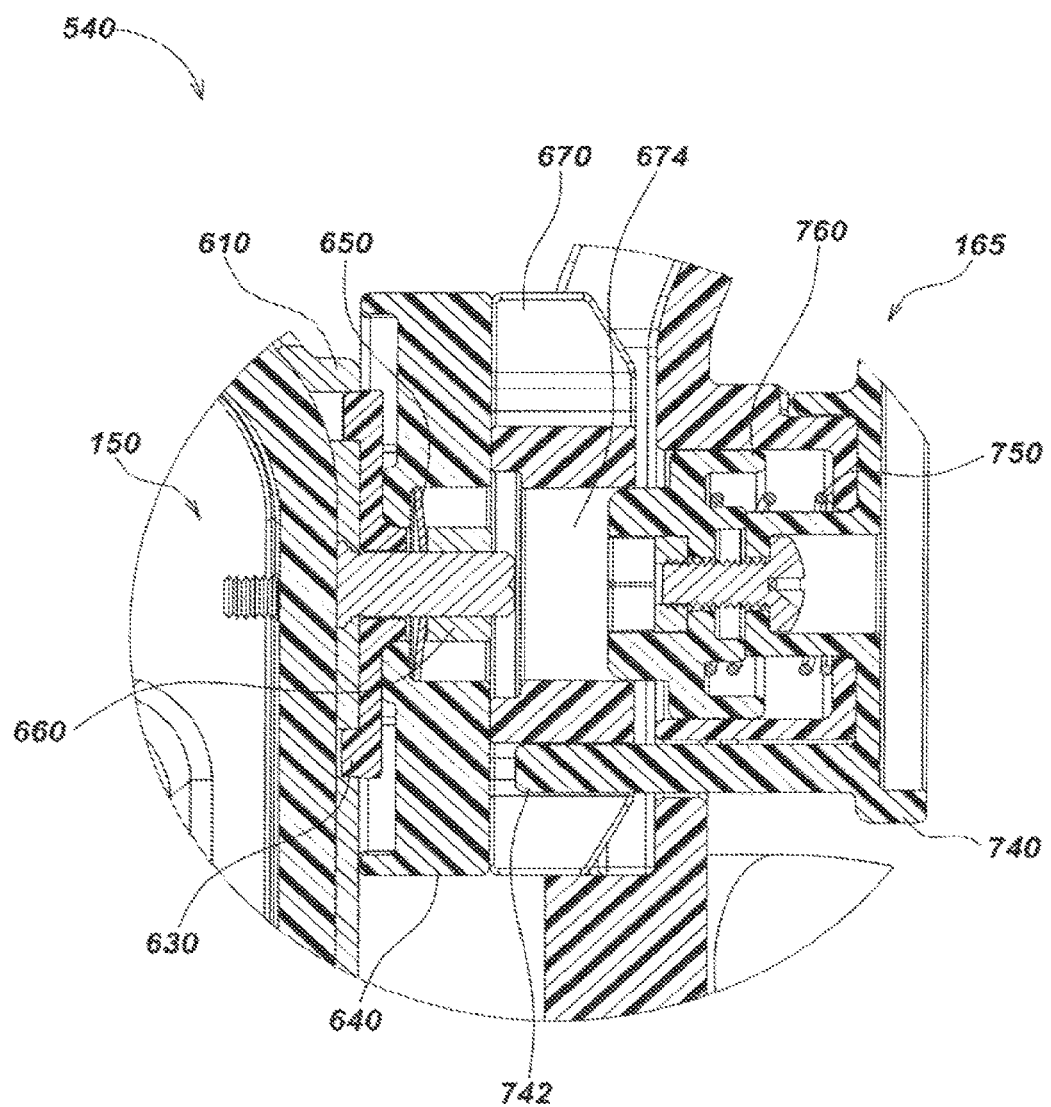
FIG. 9 is a sectional view of the pivotable docking mechanism and the docking snap and release mechanism embodiments docked together along lines 9-9 of FIG. 1A.

Turning to FIG. 9, the spring retaining docking snap element 760 may snap into place within the docking cavity 674 on the pivotable docking mechanisms 540 to dock the CCU 150 on the drum and frame 100 (FIG. 1). The CCU 150 may remain moveable and pivot via the pivotal docking mechanisms 540. Such pivoting movement may be governed by tension provided through the disk spring 650 such that the CCU 150 may be held self-supported in various angle/position orientations. When both of the knob elements 740 are pulled in an outward direction, such as illustrated in FIG. 8C, the spring retaining docking snap element 760 may dislodge from the docking cavity 674 on the pivotable docking mechanisms 540, and the CCU 150 may be pulled upwards and become undocked from the frame.

Figure 10:
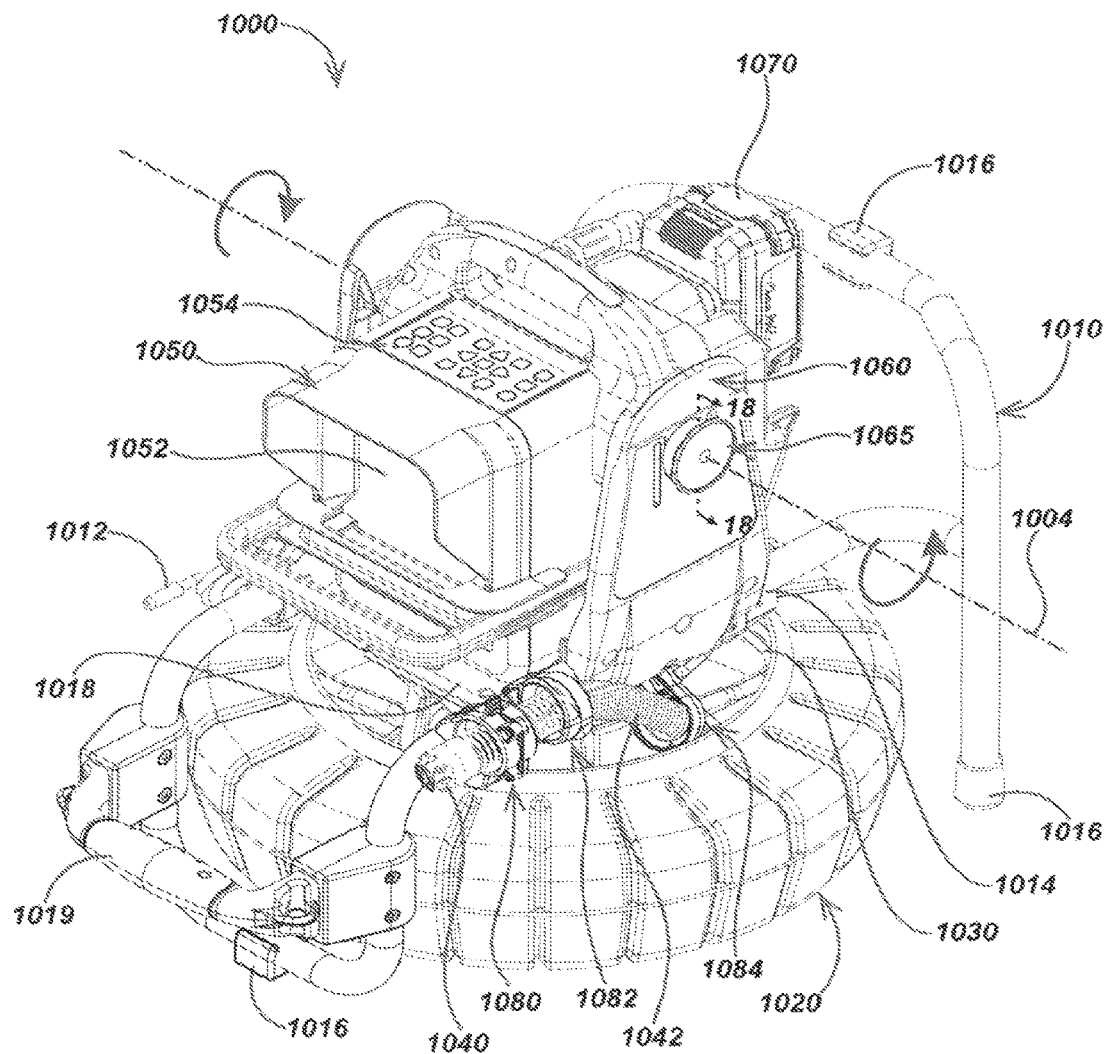
FIG. 10 is an isometric view of an alternative drum and frame with docking apparatus embodiment.

Turning to FIG. 10, an embodiment of a video inspection system 1000 including a drum assembly and a docking apparatus, in accordance with aspects of the present disclosure, is shown. Various elements as described previously herein may be used in conjunction with those described subsequently in inspection system embodiment 1000 in additional embodiments, and the various elements described subsequently may be the same as or similar to those described previously in implementation and/or function.

Inspection system embodiment 1000 may include a frame, a camera control unit (CCU) with a monitor or display, such as an LCD panel or other display element, a push-cable, a drum for storing the push-cable, an inspection camera coupled to the push-cable, as well as a docking apparatus to allow the CCU to removably couple to the frame and/or rotate relative to the frame about a pivoting or rotational axis, and/or other elements as are illustrated in the associated drawings and described herein. In operation, the CCU and display may be removably coupled to the frame such that they can be moved or rotated by an operator to adjust viewing angle or positioning of the display. The CCU and frame may be configured so that the CCU can be readily removed from the frame using a docking apparatus including a docking element assembly, latch assembly or other removably attachable retaining mechanism.

In an exemplary embodiment, a frame element 1010 may be configured to remain stationary upon the ground or other operating surface while suspending a drum element 1020 above the operating surface, such as through use of feet, legs, bars, or other ground support elements. A portion 1014 of frame 1010 may be a tube or bar section and be used to retain one side of a docking element 1060 of the docking apparatus, while another section of the frame may extend to feet 1016 as shown. The docking apparatus may include a wing-like element as shown, to which a CCU may be removable coupled, and the wing may have a pivoting or rotational axis intersecting it, about which the CCU may rotate (and or a knob or handle, which may rotate about a commonly positioned release axis), similarly to the embodiment described previously herein. Additional docking apparatus elements, such as those described subsequently, may be integral with or attached to the CCU.

A mounting platform 1018 may be formed between the frame portions 1014 and further be used to secure a drum element 1020 thereto. Other ground support configurations may also be used in alternate embodiments. In transport, the system 100 may be readily carried by a user gripping various handles located on the CCU 1050, various locations on the frame 1010, and/or a frame handle 1019. The frame 1010 may further include a cord retainer fixture 1012 (partially obscured) which may be used for storing excess amounts of the cord that may connect the drum and CCU for purposes of providing power and/or establishing a data communication link between the CCU and the inspection camera further connected to the drum and/or other system electronics, sensors, or devices. This cord may be the cord 1110 illustrated in FIG. 11 used to connect the drum element 1020 and CCU 1050. Further detail regarding an exemplary drum element may be discussed subsequently herein.

In some embodiments, there may be a counting device configured to determine and measure rotations of the drum for purposes of deriving, for instance, the quantity of push-cable dispensed and/or distance an inspection camera may have traveled from the drum. Such a counting device may be, for example, a cable counting device as discussed in co-assigned U.S. patent application Ser. No. 12/766,742, entitled PIPE INSPECTION CABLE COUNTER AND OVERLAY MANAGEMENT SYSTEM, filed Apr. 23, 2010, the content of which is incorporated by reference herein. In use, a wired or wireless data communication link may be used to update counter calibration data and/or send and/or receive other data and information.

In this configuration, the drum element 1020 coupled to the frame 1010 may be held above the ground, in a horizontal orientation (as shown in FIG. 10) or be stood on end in a vertical orientation. A user may then deploy a camera 1040 and spring 1042 coupled to push-cable 1030, which coils within the drum when stored, into a pipe or other conduit to examine the interior of the pipe or conduit by viewing images or video from the camera 1040 on a display such as the display 1052 of the CCU 1050. In use, the push-cable may, for example, be deployed into a pipe by a user which may be used to display images/video of the inspection area within the pipe as captured by the camera and shown on display 1052 of CCU 1050.

The inspection camera 1040 may be any of a variety of camera heads for inspection systems as are known or developed in the art. In an exemplary embodiment, the camera head may be a self-leveling camera head; however, various other camera heads may be used in alternate embodiments. Example details of self-leveling camera heads and associated inspection system elements as may be combined with the disclosures herein in various embodiments are described in, for example, co-assigned U.S. patent application Ser. No. 10/858,628, entitled SELF-LEVELING CAMERA HEAD, filed Jun. 1, 2004 and U.S. patent application Ser. No. 13/358,463, entitled SELF-LEVELING INSPECTION SYSTEMS AND METHODS, filed Jan. 25, 2012, the contents of which are incorporated by reference herein.

System 1000 may include a camera control unit (referred hereafter as CCU) 1050, which includes a display 1052 and user inputs and controls 1054 for operating the camera head, as well as a processing element and memory (internal to CCU 1050, not shown) for storing images and/or other information associated with a video inspection process. The system 1000 may be configured to removably dock the CCU 1050 to the frame 1010, such as with the docking element 1060 of the docking apparatus. The docking element 1060 may be further configured to allow the CCU 1050 to move relative to the frame 1010, such as via pivoting or rotational axis 1004 as shown in FIG. 10, to allow a user to adjust the viewing angle during video inspections or other operations, and or to readily remove or attach a CCU to the frame 1010.

Examples of various details of embodiments of CCUs and associated elements that may be used in conjunction with the disclosures herein in various embodiments are described in, for example, co-assigned U.S. patent application Ser. No. 13/346,668, entitled PORTABLE CAMERA CONTROLLER PLATFORM FOR USE WITH PIPE INSPECTION SYSTEM, filed Jan. 9, 2012, U.S. patent application Ser. No. 13/774,351, entitled DOCKABLE TRIPODAL CAMERA CONTROL UNIT, filed Feb. 22, 2013, U.S. patent application Ser. No. 13/941,381, entitled SELF-GROUNDING PORTABLE CAMERA CONTROL UNIT FOR USE WITH PIPE INSPECTION SYSTEM, filed Jul. 12, 2013, and U.S. patent application Ser. No. 14/216,358, entitled SMART CABLE STORAGE DRUM AND NETWORK NODE SYSTEMS & METHODS, filed Mar. 17, 2014.

The docking element 1060 may be configured to removably couple a CCU to the frame. For example, in an exemplary embodiment, the docking element may include a docking snap and release mechanism 1065 to allow a user to undock the CCU 1050 from the frame 1010 via a simple action. The CCU 1050 may be configured to pivot or move about the pivot axis 1004. The pivot axis may be in various positions above the drum 1020. In an exemplary embodiment, the pivot axis 1004 may be formed centrally between docking snap and release mechanisms 1065 on either side of the CCU 1050, and there may be a screw-in knob or other mechanism to allow rotation about a release axis, as well as retention via spring action or friction. Other release and/or pivot or rotation mechanisms may be used in alternate embodiments. In operation, the CCU 1050 may pivot or rotate about axis 1004 relative to the frame 1010 to allow a user to adjust viewing angle or protect the display from sunlight, water, or other environmental conditions.

The CCU 1050 may connect to a power source such as a battery 1070 to supply operating power. The battery 1070 may be a standard rechargeable battery or, in some embodiments, may be an intelligent or "Lucid" battery such as is described in, for example, co-assigned U.S. patent application Ser. No. 13/252,721, entitled MODULAR BATTERY APPARATUS, SYSTEMS, AND METHODS, filed in Jun. 25, 2012, the content of which is incorporated by reference herein.

In an exemplary embodiment, a camera guide and securing mechanism 1080 may secure to a section of the frame 1010. The camera guide and securing mechanism 1080, as well as one or more optional camera guides 1082 and 1084, may have a central passage configured to allow the inspection camera 1040, spring 1042, and push-cable 1030 to pass through and keep these components oriented in an appropriate direction when the system 1000 is in use. The camera guide and securing mechanism 1080, unlike the camera guides 1082 and 1084, may further be configured to lock or secure the inspection camera 1040, spring 1042, and/or push-cable 1030 in place. For instance, a lever 1950 (FIGS. 19A and 19B) may be forced into a section of the spring 1042 by a torsion spring 1960 (FIGS. 19A and 19B) securing the spring 1042, inspection camera 1040, and push-cable 1030 in place. A securing mechanism, such a camera guide and securing mechanism 1080, may prevent unwanted movement of the inspection camera 1040, spring 1042, and/or push-cable 1030. Additional details of the camera guide and securing mechanism 1080 may be discussed in subsequent paragraphs in connection with FIGS. 19A and 19B. Additional details of an embodiment of a camera guide and securing mechanism 2080 are shown in FIGS. 20-23 and FIG. 24.

Various aspects and details of embodiments of cable storage drums, CCUs, inspection cameras, and push-cables as may be combined in various embodiments with the disclosures herein are described in co-assigned U.S. patent application Ser. No. 13/787,711, entitled DUAL SENSED LOCATING SYSTEMS AND METHODS, filed on Mar. 6, 2013, U.S. patent application Ser. No. 13/346,668, entitled PORTABLE CAMERA CONTROLLER PLATFORM FOR USE WITH PIPE INSPECTION SYSTEM, filed on Jan. 9, 2012, U.S. patent application Ser. No. 13/774,351, entitled DOCKABLE TRIPODAL CAMERA CONTROL UNIT, filed on 22 Feb. 2013, U.S. patent application Ser. No. 12/704,808, entitled PIPE INSPECTION SYSTEM WITH REPLACEABLE CABLE STORAGE DRUM, filed Feb. 12, 2010, U.S. patent application Ser. No. 12/371,540, entitled PUSH-CABLES FOR PIPE INSPECTION SYSTEM, filed Feb. 13, 2009, U.S. patent application Ser. No. 13/073,919, entitled PIPE INSPECTION SYSTEM WITH JETTER PUSH-CABLE, filed Mar. 28, 2011, U.S. patent application Ser. No. 13/214,208, entitled ASYMMETRIC DRAG FORCE BEARINGS FOR USE WITH PUSH-CABLE STORAGE DRUMS, filed Aug. 21, 2011, U.S. patent application Ser. No. 12/704,808, entitled PIPE INSPECTION SYSTEM WITH REPLACEABLE CABLE STORAGE DRUM, filed Feb. 12, 2010, U.S. Pat. No. 6,545,704, U.S. Pat. No. 5,939,679, U.S. Pat. No. 6,831,679, U.S. Pat. No. 6,958,767, and U.S. Pat. No. 6,862,945. These patents and patent applications may be collectively referred to herein as the "incorporated applications." The content of each of these patents and patent applications is incorporated by reference herein in its entirety.

Figure 11:
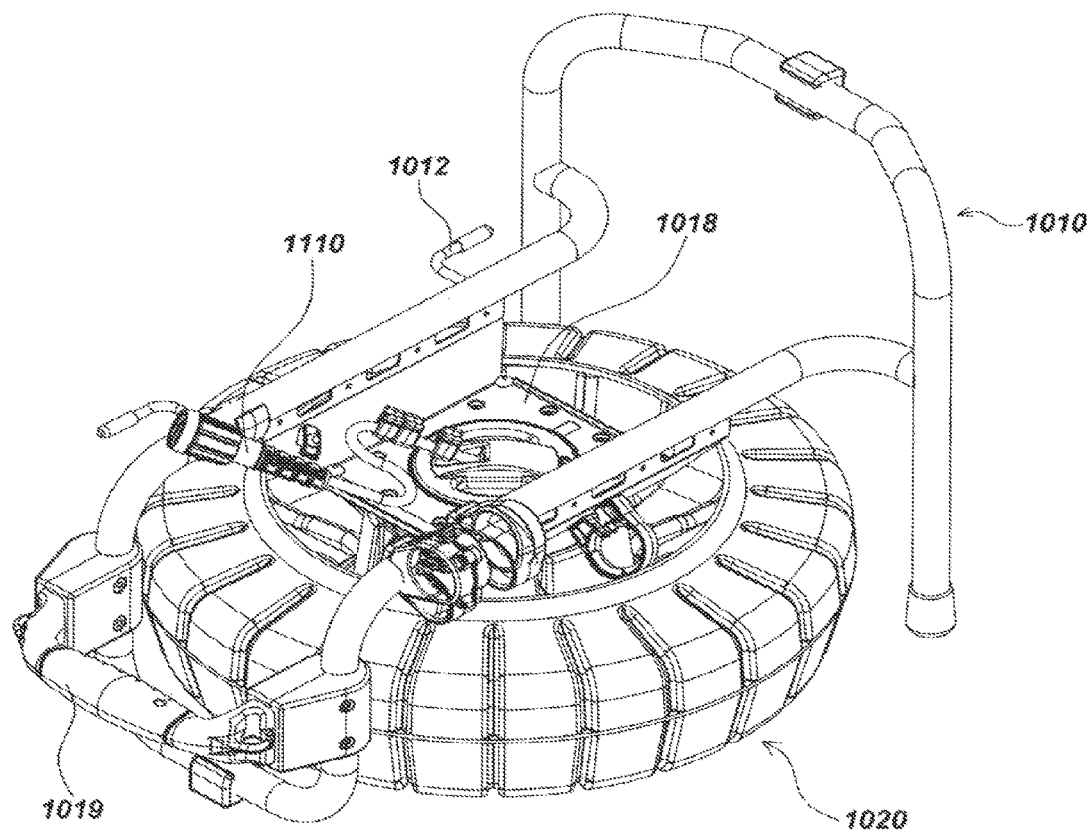
FIG. 11 is an isometric view of a drum element and frame embodiment.

Turning to FIG. 11, in the exemplary embodiment 1000, the drum element 1020 may mount to the mounting platform 1018 on the frame 1010. A cord or cable, such as the cord 1110, may be used to connect a CCU to an inspection camera for purposes of providing power and/or establishing a data communication link between the CCU and the inspection camera. For example, the CCU 1050 of FIG. 10 may connect via cord 1110 to the drum element 1020 and a connected push-cable and inspection camera such as the push-cable 1030 and inspection camera 1040 of FIG. 10. A wired or wireless data communication link may be established, such as via corresponding wired or wireless communication modules (not shown), between CCU, internal drum electronics, inspection camera and other accessory components/devices, and/or external devices or systems. Power may be provided to the inspection camera via the battery 1070 (FIG. 10) on the CCU 1050 (FIG. 10), which may be an intelligent battery as described previously herein.

In some embodiments, a drum element may include a quick release assembly for detaching the drum from the frame. Such embodiments may be more readily serviceable and/or configured for accepting other interchangeable drum assemblies.

Figure 12:
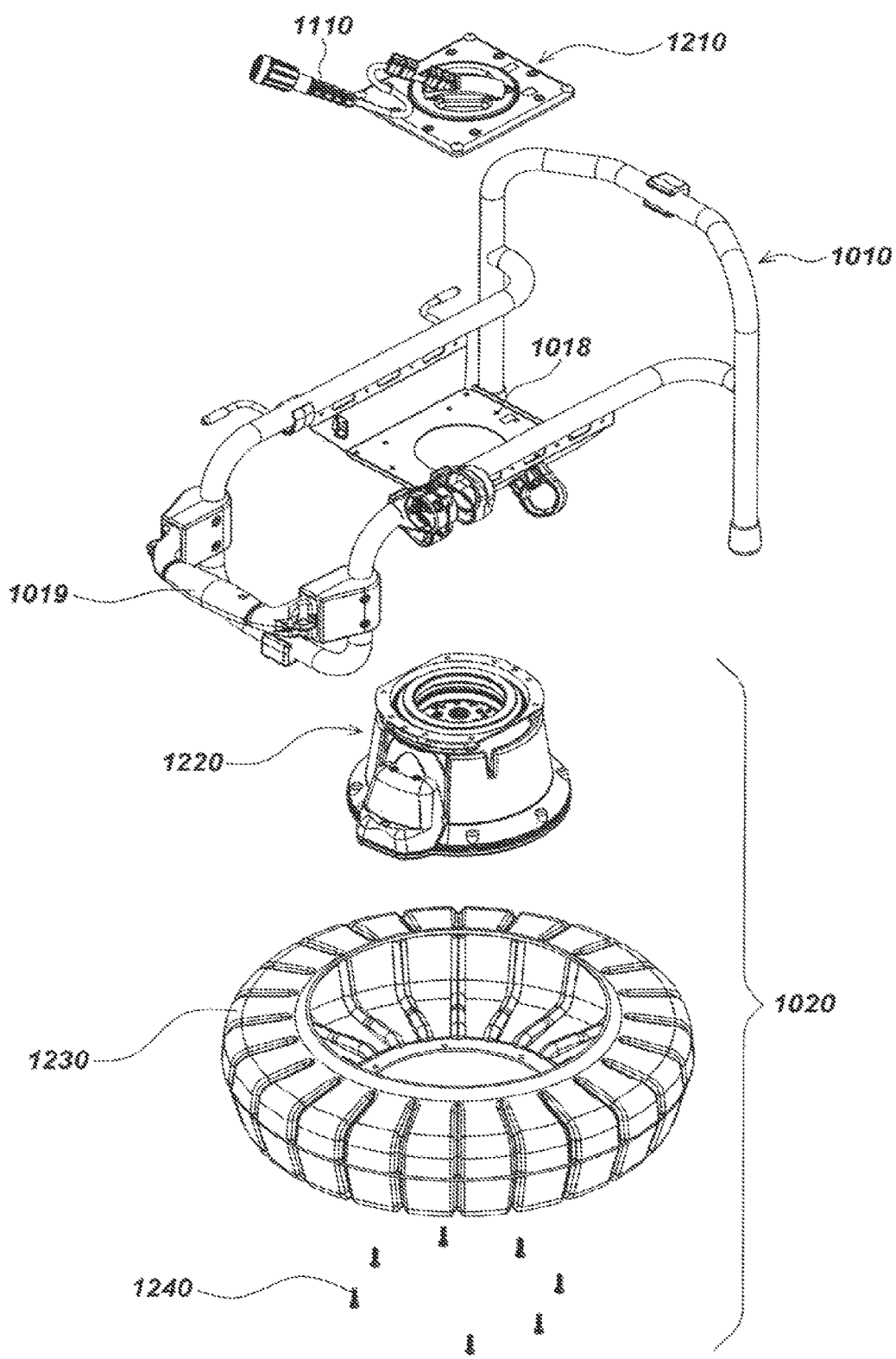
FIG. 12 is an exploded view of the embodiment of FIG. 11.

Turning to FIG. 12, the drum element 1020 may be comprised of a top hub assembly 1210, a bottom hub assembly 1220, and a drum casing 1230 that may be used to store and dispense push-cable, spring, and inspection camera such as the push-cable 1030, spring 1042 and inspection camera 1040 of FIG. 10. The top hub assembly 1210 may secure about the top of the mounting platform 1018 such that components centrally on the top hub assembly 1210 may fit through an opening centrally formed on the mounting platform 1018 of the frame 1010 and connect with components on the bottom hub assembly 1220 situated on the other side of the mounting platform 1018. The bottom hub assembly 1220 may secure both to the drum casing 1230 via screws 1240. The bottom hub assembly 1220 may be configured to allow rotations of the drum casing 1230 during dispensing and/or retracting of push-cable while components of the top hub assembly 1210 may remain stationary. A bearing mechanism within the bottom hub assembly 1220 may facilitate such rotations and, in some embodiments, govern the drag or required force of such rotations in one or more directions.

Figure 13:
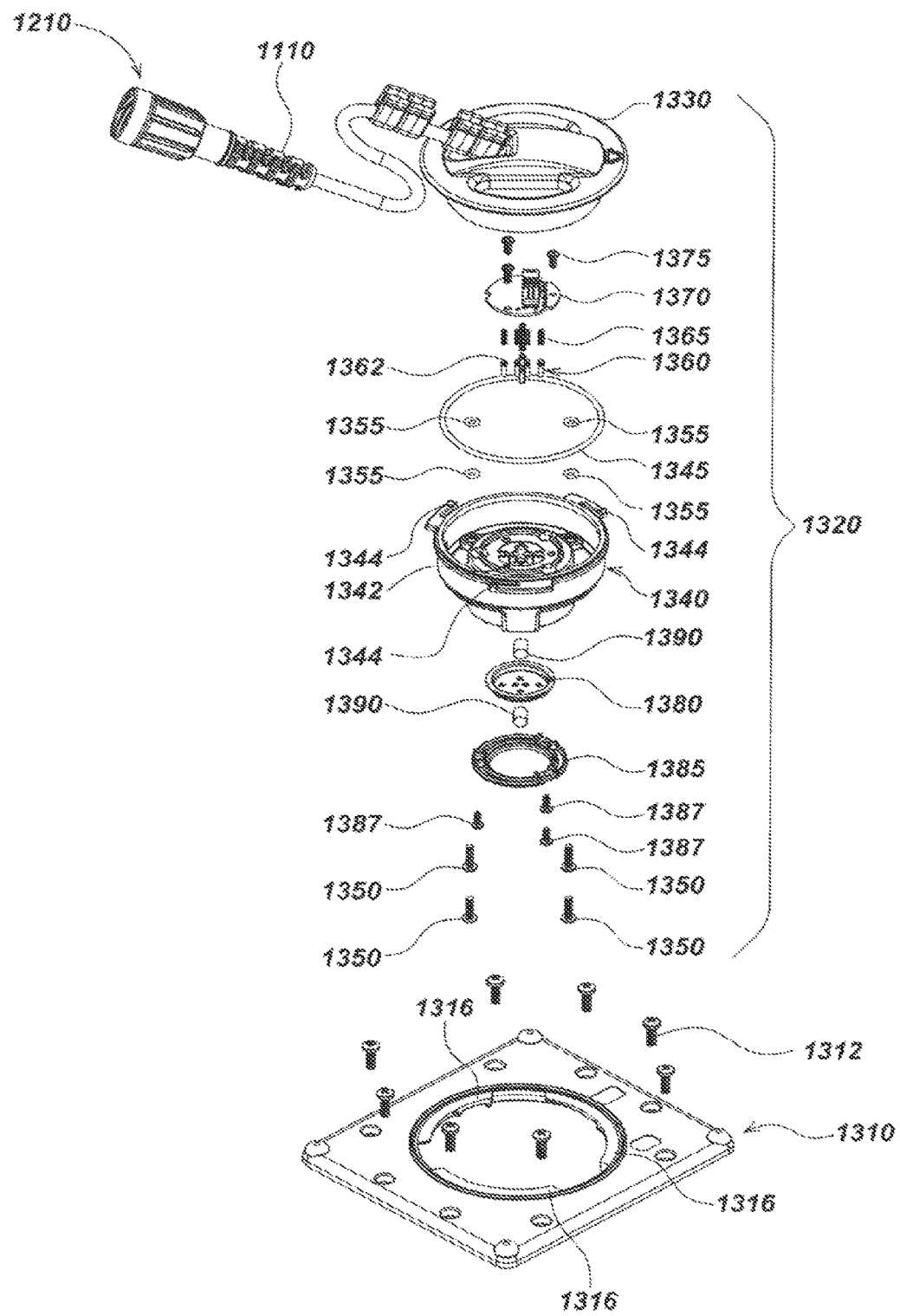
FIG. 13 is an exploded view of a top hub assembly embodiment.
Figure 14:
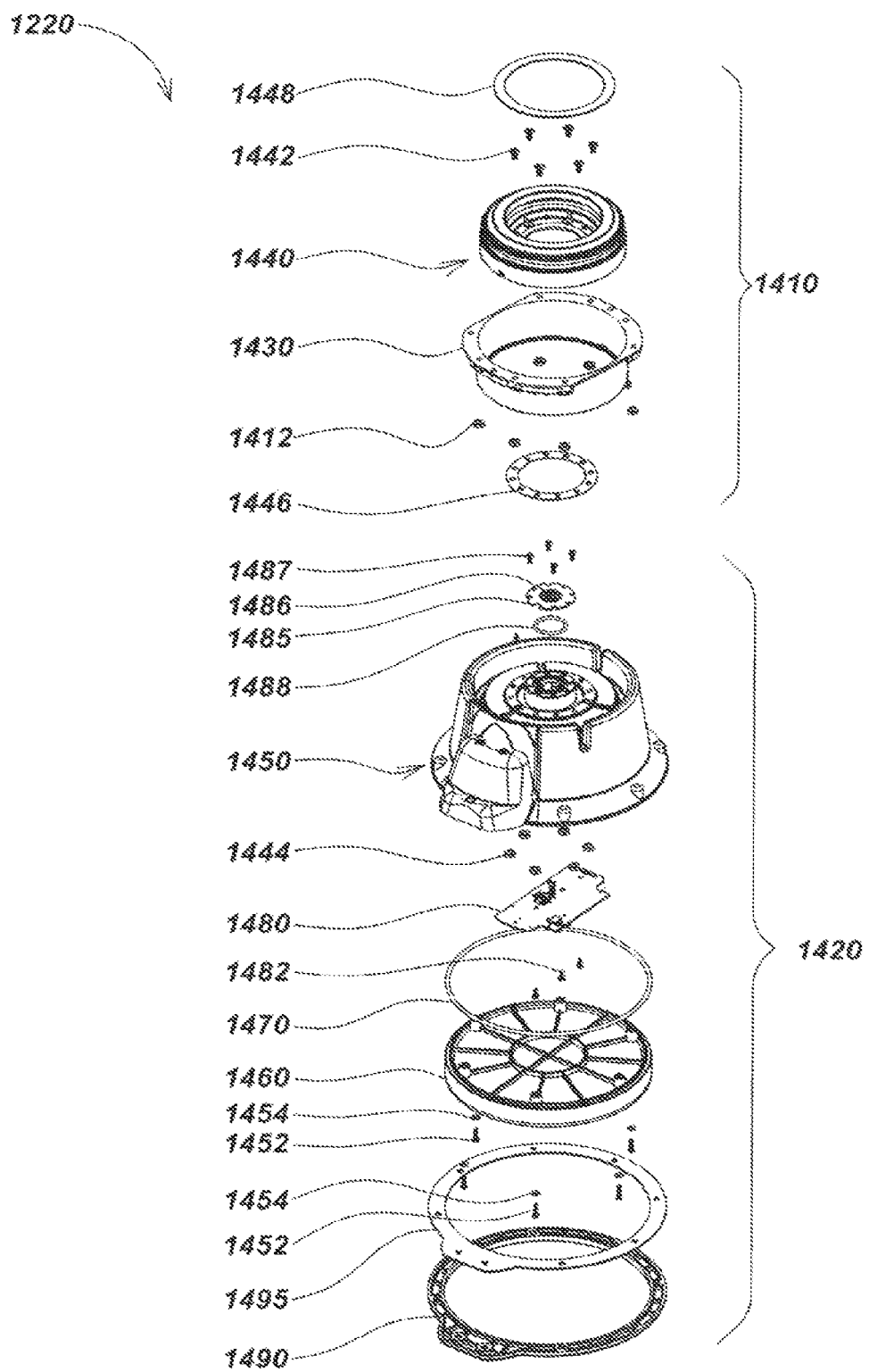
FIG. 14 is an exploded view of a bottom hub assembly embodiment.

Turning to FIG. 13, the top hub assembly 1210 may further be comprised of a platform mounting plate 1310 formed with a central opening that may secure to the top of the mounting platform 1018 via bolts 1312 and nuts 1412 (FIG. 14). The bolts 1312 may further secure a bearing retainer subassembly 1410 as illustrated in FIG. 14 to the opposite side of the mounting platform 1018 (FIG. 11) from the platform mounting plate 1310. The central opening on the platform mounting plate 1310 and the central opening on the mounting platform 1018 (FIG. 11) may align when assembled and be configured to accommodate a plug subassembly 1320. The plug subassembly 1320 may further be comprised of a top plug housing element 1330 and bottom plug housing element 1340.

The top plug housing element 1330 and bottom plug housing element 1340 may secure together via screws 1350. In assembly, an O-ring 1345 may be seated between the top plug housing element 1330 and bottom plug housing element 1340. A series of seals 1355, each of which may correspond to one of the screws 1350, may seat within top plug housing element 1330. The o-ring 1345 and seals 1355 may aid in providing protection to internal components from moisture or other potentially damaging external elements.

The bottom plug housing element 1340 may be formed with a series of central pin retaining features 1342 configured to house and retain a series of pins 1360 in assembly. The pins 1360 may be formed such that the head 1362 of each pin is of greater diameter than the pin's 1360 lower section. The lower section of the central pin retaining features 1342 may also be of smaller diameter but dimensioned to allow the lower section of each pin 1360 to pass through while the head 1362 of each pin 1360 may not thus retaining each pin 1360 within the central pin retaining feature 1342. A series of springs 1365 may seat onto the head 1362 of each pin 1360 and further connect to traces on a PCB 1370 and may provide connection between the pins 1360 and the PCB 1370 for purposes of providing power and/or establishing a data communication link. In use, the springs 1365 may also provide force holding the pins 1360 firmly to circular traces 1486 (FIG. 14) on a connector element 1485 (FIG. 14) found in the bottom hub assembly 1220.

The PCB 1370 may secure atop the bottom plug housing element 1340 via screws 1375. The top plug housing element 1330 may retain one end of the cord 1110. Wiring within the cord 1110 may secure to the PCB 1370 and may function to provide a connection from a CCU, such as the CCU 1050 of FIG. 10, to the plug subassembly 1320 and ultimately provide such a connection to an inspection camera for purposes of providing power and/or establishing a wired or wireless data communication link.

A seal element 1380 may seat centrally onto the bottom of the bottom plug housing element 1340 allowing the lower section of the pins 1360 to pass through holes therein. The seal element 1380 may attach to the bottom plug housing element 1340 via a seal retainer element 1385 and screws 1387. The seal element 1380 may aid in providing protection to internal components from moisture or other potentially damaging external elements.

One or more magnets, such as the magnets 1390, may be seated within and along the circumference of the bottom section of the bottom plug housing element 1340. In use, the magnets 1390 may be positioned such that corresponding magnetic sensors, which may be hall-effect sensors, configured within the bottom hub assembly 1220 (FIG. 12) to rotate with the drum, may further be configured to detect and/or measure rotations of the drum. Such data may be used to derive, for instance, quantity of push-cable dispensed and/or distance an inspection camera may have traveled from the drum. Such a counting device may be, for example, a cable counting device as disclosed in co-assigned U.S. patent application Ser. No. 12/766,742, entitled PIPE INSPECTION CABLE COUNTER AND OVERLAY MANAGEMENT SYSTEM, filed Apr. 23, 2010, the content of which is incorporated by reference herein. In use, the data communication link may be utilized to update counter calibration data.

When assembled, the plug subassembly 1320 may secure to the platform mounting plate 1310. A series of bottom plug housing element keying features 1344 on the bottom plug housing element 1340 may key with a series of corresponding platform mounting plate keying features 1316 on the platform mounting plate 1310 to hold the plug subassembly 1320 firmly to the platform mounting plate 1310. A rotational force in a counter clockwise direction applied to the plug subassembly 1320 may free the plug subassembly 1320 from the platform mounting plate 1310 and may readily provide access to components within. Such a configuration may be particularly advantageous for performing maintenance to such components.

Turning to FIG. 14, the bottom hub assembly 1220 may further be comprised of a bearing mount subassembly 1410 and push-cable mount subassembly 1420. The bearing mount subassembly 1410 may further be comprised of a bearing mount housing element 1430 that may secure to the bottom of the mounting platform 1018 (FIG. 11) via bolts 1312 (FIG. 13) and nuts 1412. A bearing mechanism 1440 may seat within and key to the bearing mount housing element 1430. The bearing mechanism 1440 may further secure to a top push-cable mount housing subassembly 1450 on the push-cable mount subassembly 1420 via bolts 1442 and nuts 1444 with a sealing ring 1446 positioned between the bearing mechanism 1440 and top push-cable mount housing subassembly 1450.

Figure 15:
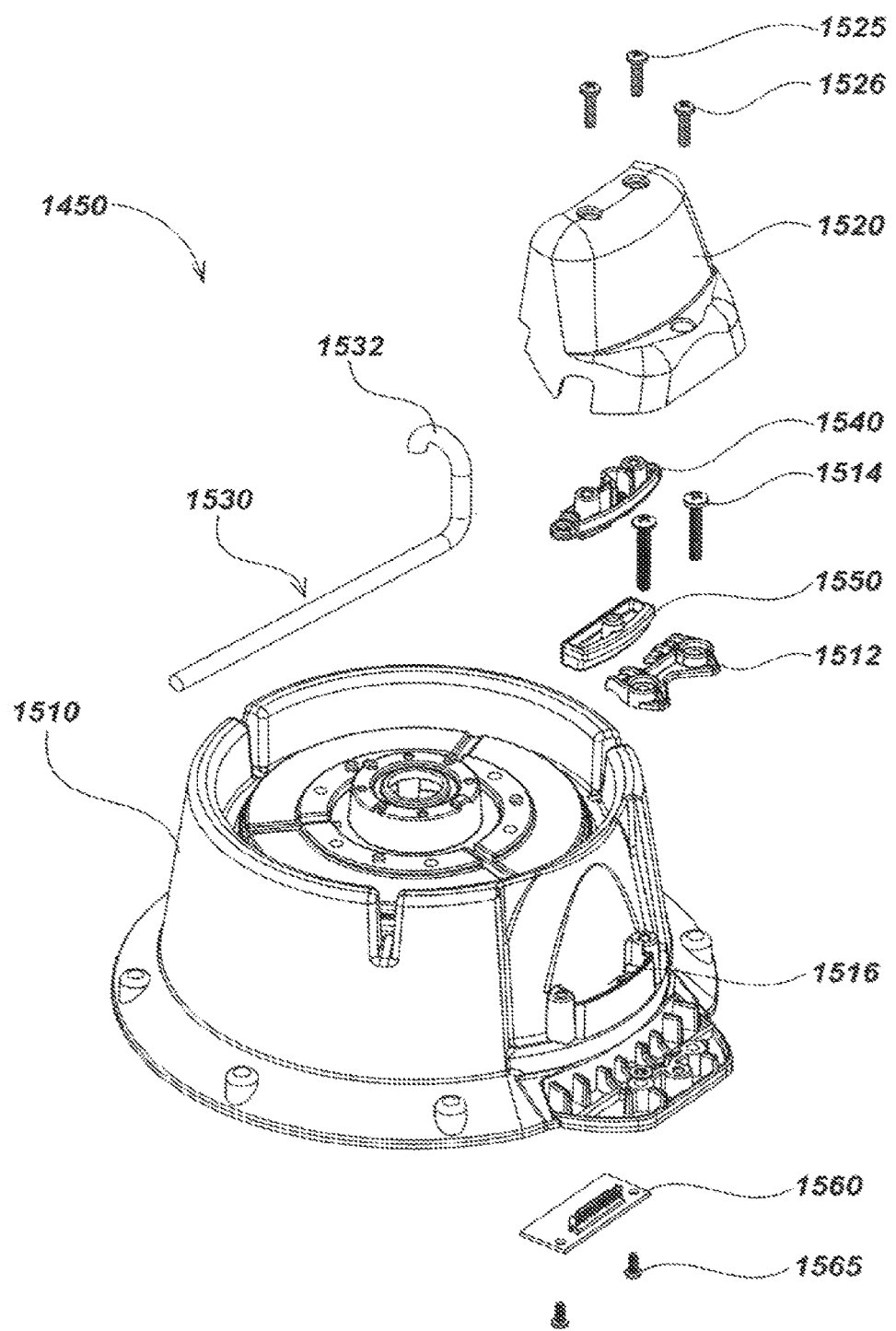
FIG. 15 is an exploded view of a top push-cable mount housing subassembly embodiment.

The bearing mechanism 1440 may be configured to allow rotations of the push-cable mount subassembly 1420 during dispensing and/or retracting of a push-cable that may further secure to the top push-cable mount housing subassembly 1450 as illustrated in FIG. 15. The bearing mechanism 1440 may be further configured to govern rotations in one direction. Details of embodiments of bearing mechanisms configured to govern rotations in one direction that may be used in conjunction with the disclosures herein various embodiments are disclosed in, for example, co-assigned U.S. patent application Ser. No. 13/214,208, entitled ASYMMETRIC DRAG FORCE BEARINGS FOR USE WITH PUSH-CABLE STORAGE DRUMS, filed in Aug. 10, 2010, the content of which is incorporated by reference herein. A seal ring 1448 may seat between the bearing mechanism 1440 and the mounting platform 1018 (FIG. 11) in assembly.

The push-cable mount subassembly 1420 may further be comprised of a bottom push-cable mount housing 1460 that may secure within the bottom section of the top push-cable mount housing subassembly 1450 via screws 1452. A series of seals 1454 may be used with each screw 1452 as well as an o-ring 1470 positioned between the top push-cable mount housing subassembly 1450 and bottom push-cable mount housing 1460 to aid in providing protection to internal components from moisture and/or other potentially damaging external elements.

A PCB 1480 may secure within the top push-cable mount housing subassembly 1450 via screws 1482. The PCB 1480 may connect via wiring or other connector for purposes of providing power and/or establishing a data communication link to a push-cable that may further secure to the top push-cable mount housing subassembly 1450 as illustrated in FIG. 15 as well as to circular traces 1486 on a connector element 1485. The connector element 1485 may secure centrally to the top of the top push-cable mount housing subassembly 1450 via screws 1487. An o-ring 1488 may seat between the connector element 1485 and top push-cable mount housing subassembly 1450 to provide a seal to internal components housed within the push-cable mount subassembly 1420.

In assembly, the drum casing 1230 (FIG. 12) may secure to the bottom circumference of the top push-cable mount housing subassembly 1450 via screws 1240 (FIG. 12). A flange element 1490 and flange seal 1495 may secure between the drum casing 1230 (FIG. 12) and the top push-cable mount housing subassembly 1450. The flange element 1490 and flange seal 1495 may be largely ring shaped with a node along a portion of the circumference to match a node formed along one side of the top push-cable mount housing subassembly 1450.

Turning to FIG. 15, the top push-cable mount housing subassembly 1450 may further be comprised of a push-cable mount housing element 1510 and a node housing element 1520. The node housing element 1520 may secure to the push-cable mount housing element 1510 via rear screws 1525 and a front screw 1526. A push-cable end portion 1530 may secure to a cable retention element 1512 on the push-cable mount housing element 1510. Screws 1514 may be configured to be tightened and hold the push-cable end portion 1530 in place between the cable retention element 1512 and the bottom section of the node on the push-cable mount housing element 1510. A section 1532 of the push-cable end portion 1530 may be stripped to access wiring within. The wiring may sandwich between a top wiring bracket element 1540 and bottom wiring bracket element 1550. The top wiring bracket element 1540 and bottom wiring bracket element 1550 may further secure onto a mount housing passage feature 1516 on the push-cable mount housing element 1510 via rear screws 1525. The wiring may further connect to a wiring connector 1560. The wiring connector 1560 may further secure to the push-cable mount housing element 1510 via screws 1565. In assembly wiring (not illustrated) may connect the wiring connector 1560 and PCB 1480 (FIG. 14) for purposes of providing power and/or establishing a data communication link.

Figure 16A:
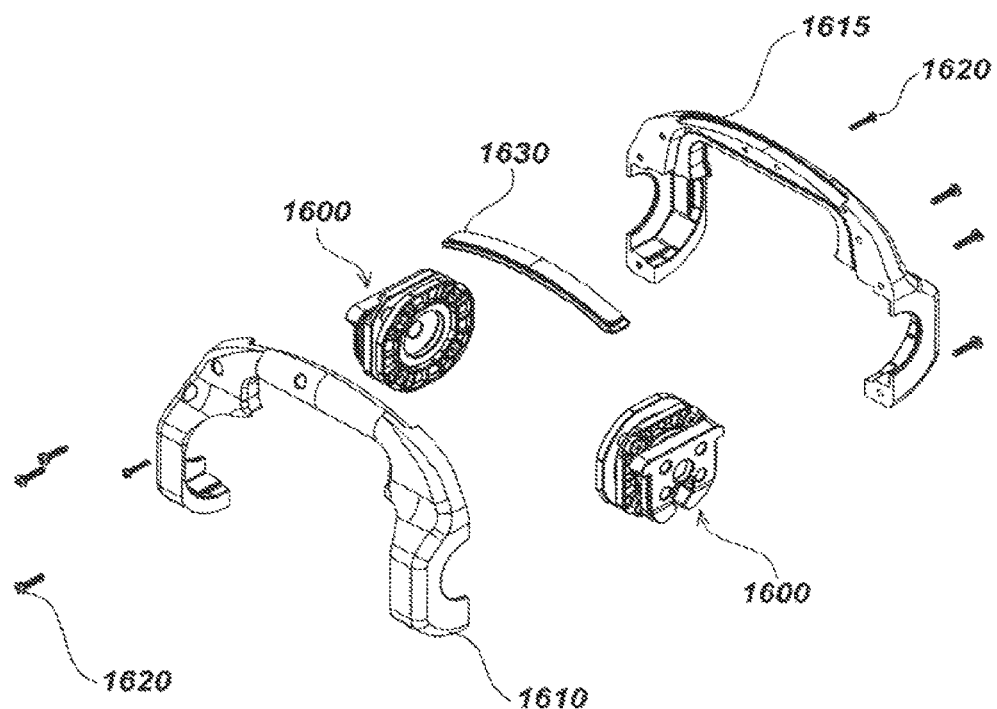
FIG. 16A is a partially exploded view of an alternative docking and pivot mechanism embodiment and handle retainer element embodiment.
Figure 16B:
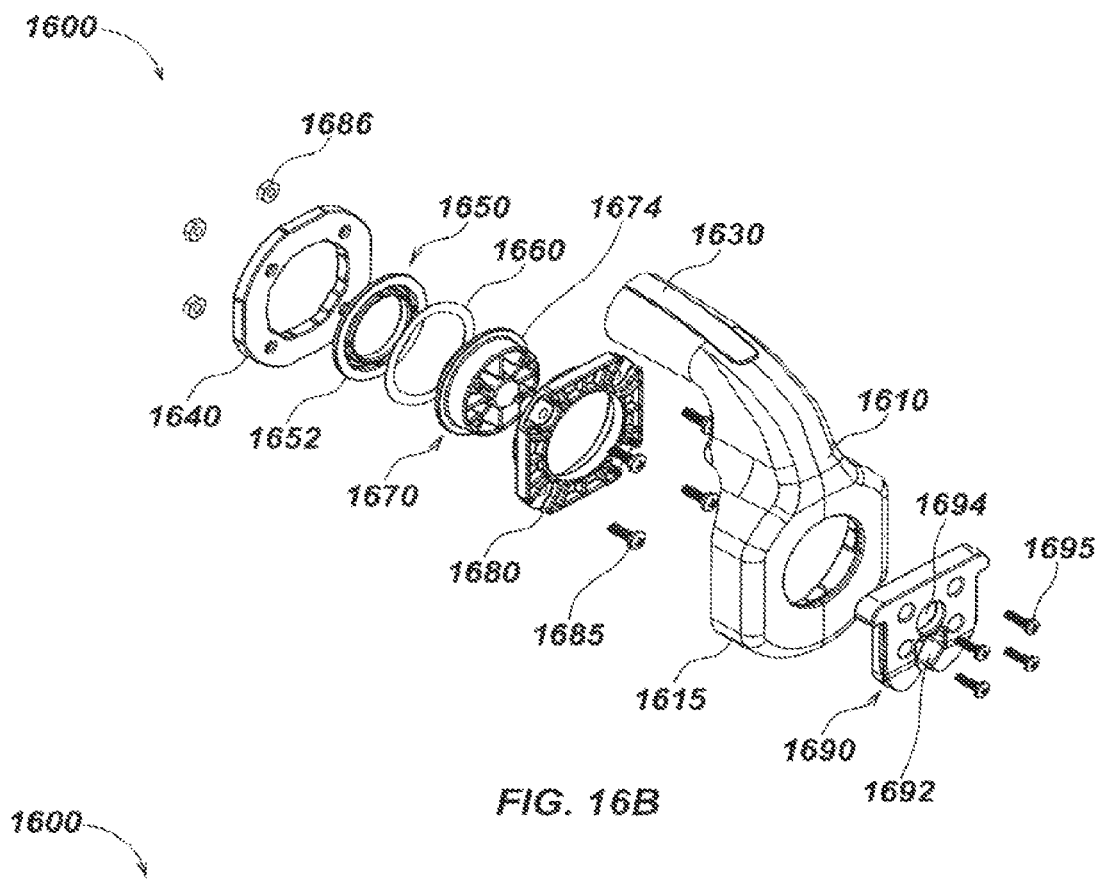
FIG. 16B is a different partially exploded view of an alternative docking and pivot mechanism embodiment and handle retainer element embodiment.
Figure 16C:
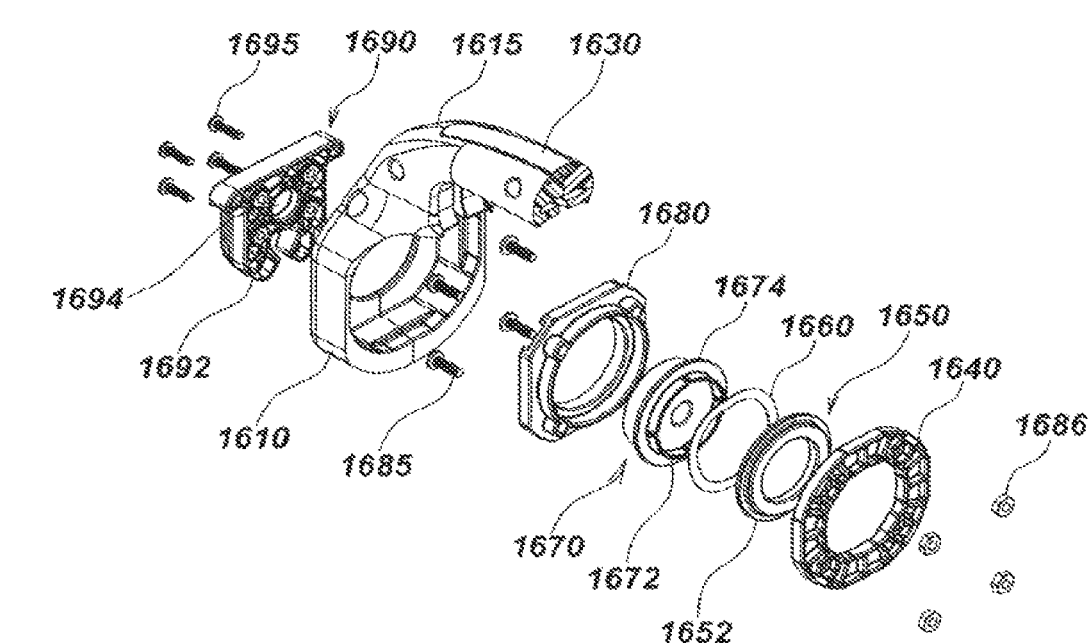
FIG. 16C is the partially exploded view of the embodiment of FIG. 16B taken from the opposite side.

Turning to FIGS. 16A, 16B, and 16C an alternative docking apparatus including a docking and pivot mechanism embodiment 1600 is illustrated. This docking and pivot mechanism may secure to either side of a CCU, such as the CCU 1050 of FIG. 10, via a front handle retainer element 1610 and rear handle retainer element 1615 that secure and entrap within the handle on a CCU via screws 1620. The docking and pivot mechanism 1600 may, in part, seat within front handle retainer element 1610 and rear handle retainer element 1615 and between the CCU and assembled handle retainers. A cushion element 1630 may adhere to the top section of the assembled front handle retainer element 1610 and rear handle retainer element 1615, providing enhanced comfort to a user during use.

Turning to FIGS. 16B and 16C, the portion of the docking and pivot mechanism 1600 that may seat within the front handle retainer element 1610 and rear handle retainer element 1615 in assembly may be comprised of an inner plate element 1640 formed with a central opening dimensioned to seat an inner wave spring holder element 1650 partially within. A lip feature 1652 on the inner wave spring holder element 1650 may prevent the inner wave spring holder element 1650 to seat fully within the central opening on the inner plate element 1640. A wave spring 1660 may be positioned between the inner wave spring holder element 1650 and an outer wave spring holder element 1670. A wave spring retention feature 1672 (FIG. 16C) may be formed along one side of the outer wave spring holder element 1670 that may be of smaller diameter and be made to pass centrally through the wave spring 1660 and a central opening on the inner wave spring holder element 1650.

A lip feature 1674 formed on the outer wave spring holder element 1670 may catch on the inner side of an outer plate element 1680 as the outer wave spring holder element 1670 seats within and passes through a circular opening formed through the outer plate element 1680. The outer plate element 1680 may secure to the inner plate element 1640 via bolts 1685 and corresponding nuts 1686. The outer wave spring holder element 1670 may rotate about an axis while the outer plate element 1680 and inner plate element 1640 may be seated within the handle retainer element 1610 and 1615 and held stationary thereto. The wave spring 1660 may be compressed between the inner wave spring holder element 1650 and outer wave spring holder element 1670 to provide sufficient tension to an attached CCU that the CCU may be positioned or angled by a user and the CCU may hold to that position or angle.

A docking plate 1690 may secure to the outer wave spring holder element 1670 via screws 1695 and be positioned outside the handle retainer element 1610 and 1615. The docking plate 1690 may be formed with a reset gap feature 1692 which may be configured to guide components on a docking snap and release mechanism 1065 (FIG. 10) to automatically reset into a docking ready state upon undocking a CCU. The reset gap feature 1692 may be shaped with a small central opening below a larger void. Inward sloping sides around this void may guide a docking reset prong 1742 (FIG. 17A) on the docking snap and release mechanism 1065 (FIG. 17A) towards the small central opening and actuate the resetting into the docking ready state when a CCU is made to undock.

When in a docked state, a docking cavity 1694 formed centrally on the docking plate 1690 may accommodate the end of a spring retaining docking snap element 1760 (FIG. 17A) on the docking snap and release mechanism 1065 (FIG. 17A) and dock a CCU, such as the CCU 1050 (FIG. 10), to a docking element, such as the docking element 1060 (FIG. 10). Additional details regarding the various docking components as well as the automatic resetting or pre-loading of the device into a docking ready state, and other docking functions, are described subsequently herein.

Figure 17A:
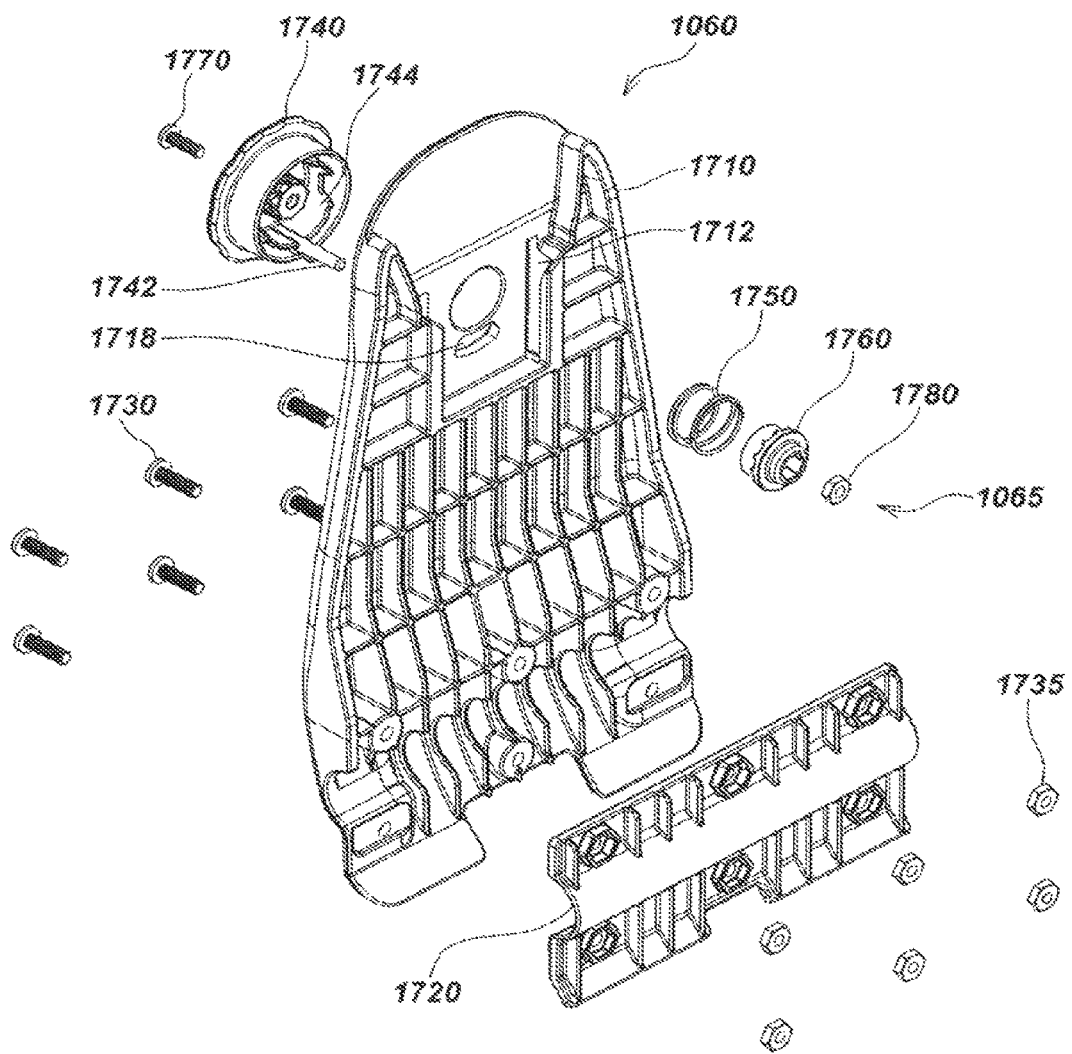
FIG. 17A is an exploded view of a docking apparatus embodiment.
Figure 17B:
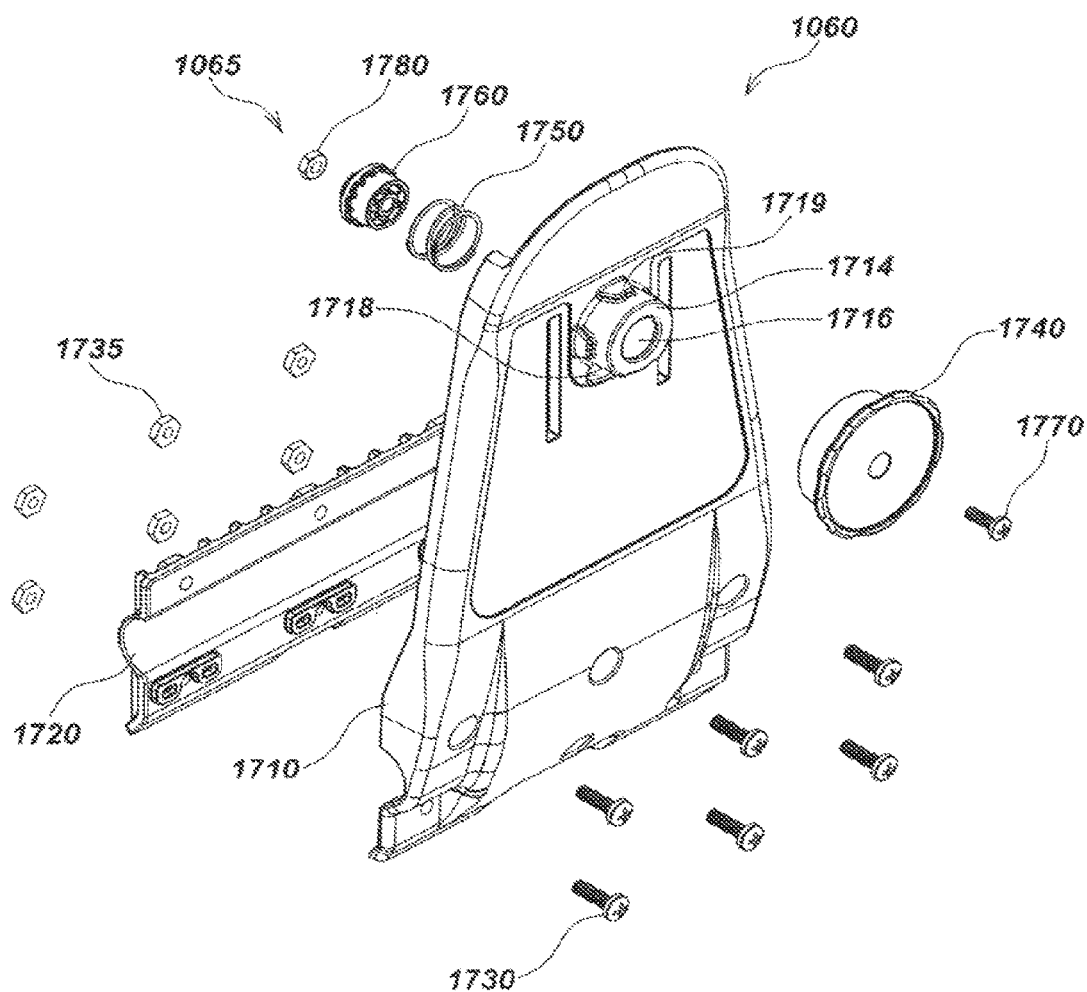
FIG. 17 B is an exploded view of the docking apparatus embodiment of FIG. 17A from a different perspective.

Turning to FIGS. 17A and 17B, the docking element 1060 with attached docking snap and release mechanism 1065 may further be comprised of a set of docking bracket arms 1710 and bottom bracket element 1720 that attach to the frame element 1010 (FIG. 10) via bolts 1730 and nuts 1735. The inward facing side of each docking bracket arm 1710, as illustrated in FIG. 17A, may be formed with a guide feature 1712 configured to guide corresponding pivotable docking mechanisms 1600 (FIG. 16A) and attached CCU 1050 (FIG. 10) during docking and undocking of the CCU 1050 (FIG. 10). As illustrated in FIG. 17B, the outward facing side of each docking bracket arm 1710 may be formed with a release nubbin 1714 and hole feature 1716 about which the various components of the docking snap and release mechanism 1065 may be seated in assembly.

A knob element 1740 of the docking snap and release mechanism 1065 may seat onto the release nubbin 1714 while a spring 1750 seated onto a spring retaining docking snap element 1760 may sit partially protruding from within the cavity formed along the inward facing side of each docking bracket arm 1710 by the release nubbin 1714. A bolt 1770 may feed centrally through the knob element 1740, the hole feature 1716 formed centrally through the release nubbin 1714, the spring 1750 seated onto the spring retaining docking snap element 1760, and secure via nut 1780 which may further seat within the back of the spring retaining docking snap element 1760 in assembly.

When assembled, a docking reset prong 1742 (FIG. 17A) formed pointing inwards along the circumference on each knob element 1740 may fit into and be provided room to move back and forth within a groove 1718 formed through each docking bracket arm 1710. The spring 1750 may create tension such that a user may pull the knob element 1740 outward and rotate. When the knob element 1740 is pulled outward, the spring retaining docking snap element 1760 may also move outward and seat further within the cavity formed along the inward facing side of each docking bracket arm 1710 by the release nubbin 1714.

When in a docking ready state, a series of release nubbin keying teeth 1719 (FIG. 17B) formed on the release nubbin 1714 may key between a series of knob keying teeth 1744 (FIG. 17A) formed onto the knob element 1740. The docking reset prong 1742 may be positioned centrally such that when a CCU such as the CCU 1050 of FIG. 10 is docked, the docking reset prong 1742 may align to the opening on the reset gap feature 1692 (FIG. 16B).

When the knob element 1740 is pulled in an outward direction and rotated about the release axis, the knob keying teeth 1744 (FIG. 17A) formed onto the knob element 1740 may rest upon the release nubbin keying teeth 1719 (FIG. 17B) formed on the release nubbin 1714. In such a state, the docking reset prong 1742 on the knob element 1740 may move within the reset gap feature 1692 (FIG. 16B) such that the docking reset prong 1742 no longer aligns with the opening on the reset gap feature 1692 (FIG. 16B). When a CCU, such as the CCU 1050 of FIG. 10, becomes undocked, the docking reset prong 1742 may be forced to slide along the sides of the reset gap feature 1692 (FIG. 16B) until the docking reset prong 1742 is made to align with the opening on the reset gap feature 1692 (FIG. 16B), thus automatically resetting into a docking ready state upon undocking the CCU 1050.

Figure 18:
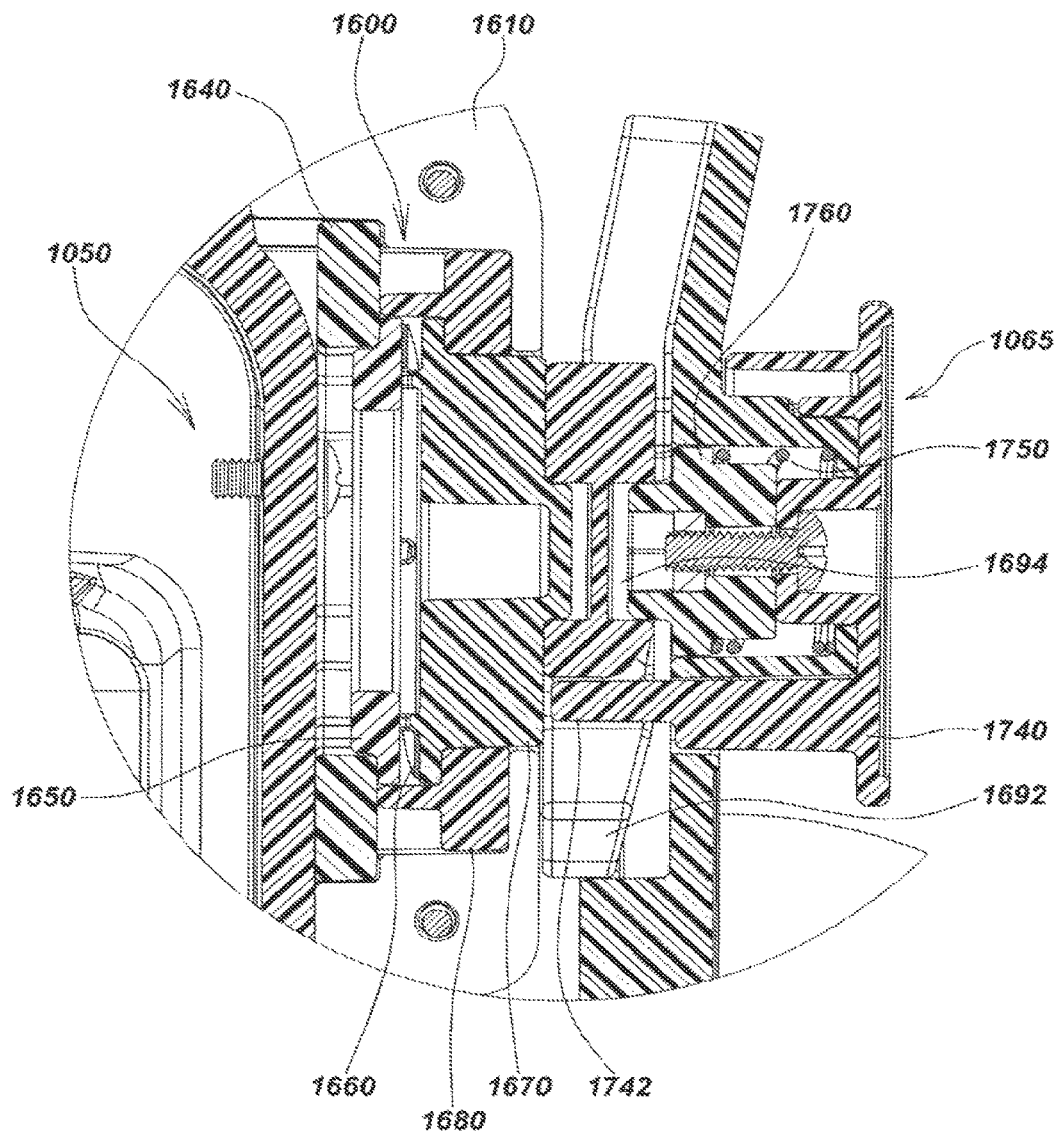
FIG. 18 is a sectional view of the pivotal docking mechanism embodiment and the docking snap and release mechanism embodiment docked together along lines 18-18 of FIG. 10.

Turning to FIG. 18, the spring retaining docking snap element 1760 may snap into place within the docking cavity 1694 on the pivotable docking mechanisms 1600 to dock the CCU 1050 on the system 1000 (FIG. 10). The CCU 1050 may remain moveable and be permitted to rotate or pivot via the pivotal docking mechanisms 1600. Such pivoting may be governed by tension provided through the wave spring 1660 such that the CCU 1050 is held self-supported in various angle/position orientations. When both of the knob elements 1740 are pulled in an outward direction, the spring retaining docking snap element 1760 may become dislodged from the docking cavity 1694 on the pivotable docking mechanisms 1600, and the CCU 1050 may be pulled upwards and become undocked.

Figure 19A:
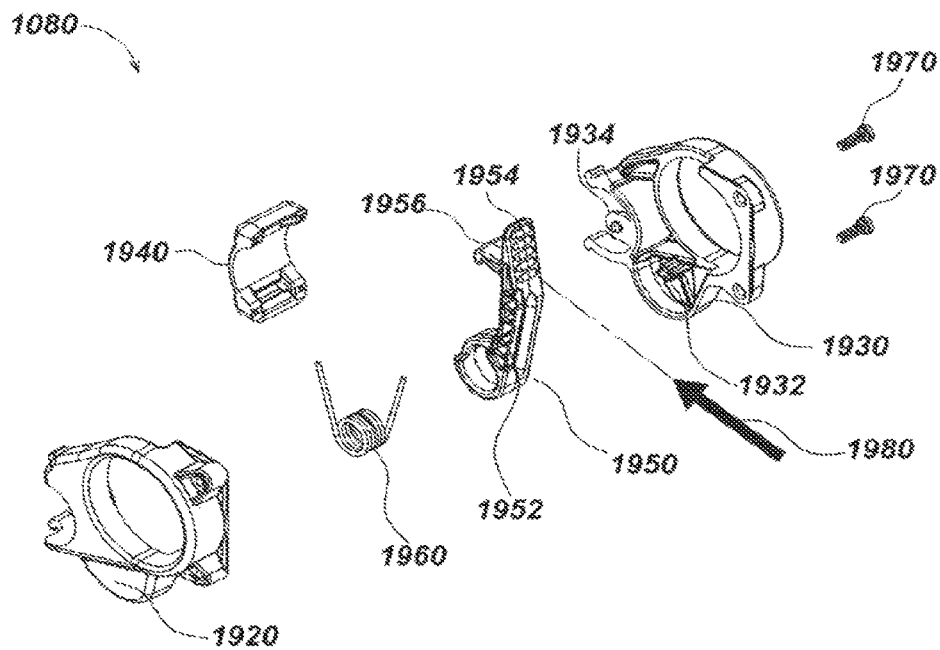
FIG. 19A is an exploded view of a camera guide and securing mechanism embodiment.
Figure 19B:
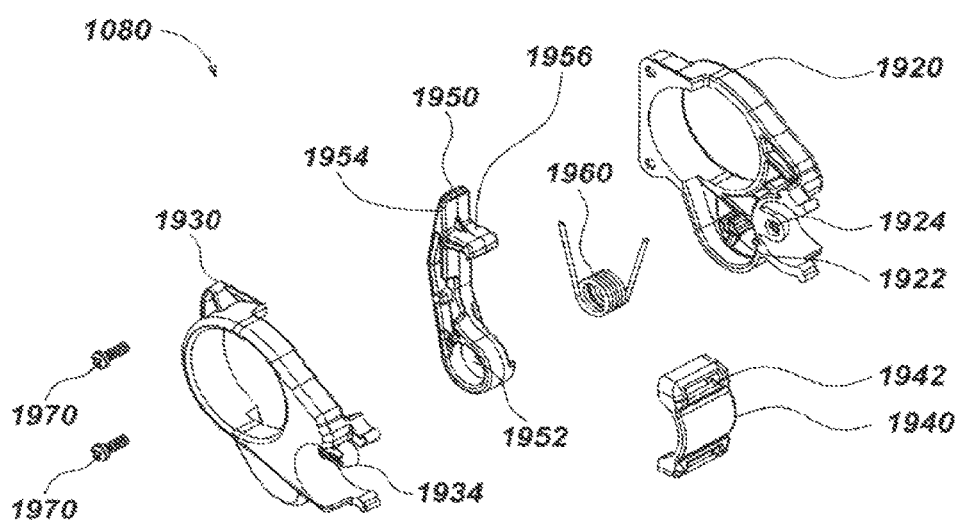
FIG. 19B is an exploded view of a camera guide and securing mechanism embodiment of FIG. 19B from the opposite direction.

Turning to FIGS. 19A and 19B, additional details of an embodiment of camera guide and securing mechanism 1080 are shown. Camera guide and securing mechanism 1080 may further be comprised of a front housing element 1920, a back housing element 1930, a frame mounting element 1940, a lever 1950, a torsion spring 1960, and a series of screws 1970. In assembly, the base of the torsion spring 1960 may seat within an opening 1952 on the lever 1950 while one arm of the torsion spring 1960 may seat along the length of the lever 1950. The opposite arm of the torsion spring 1960 may seat onto and secure to a section of the front housing element 1920 such that the torsion spring 1960 is compressed and tension is applied to the lever 1950. In use, this tension may secure an inspection camera, spring, and/or push-cable which may be the inspection camera 1040, spring 1042, and/or push-cable 1030 of FIG. 10. The front housing element 1920 and back housing element 1930 may secure together with screws 1970 such that the lever 1950 and torsion spring 1960 are secured between. The torsion spring 1960 and lever 1950 may further be seated about a front housing post 1922 (FIG. 19B) formed on the front housing element 1920 and a back housing post 1932 (FIG. 19A) formed on the back housing element 1930.

A top lever section 1954 and securing clip feature 1956 on the lever 1950 may extend beyond the front housing element 1920 and back housing element 1930 such that in use a user may apply a force in direction 1980 to the top lever section 1954, releasing tension to an inspection camera, spring, and/or push-cable which may be the inspection camera 1040, spring 1042, and/or push-cable 1030 of FIG. 10. When a force in direction 1980 sufficient to push lever 1950 back all the way towards the frame mounting element 1940 is applied to the lever 1950, the securing clip feature 1956 may secure to a clip retainer feature 1942 (19B) on the frame mounting element 1940 and allow the lever 1950 and camera guide and securing mechanism 1080 to remain in an open state and allow the inspection camera 1040, spring 1042, and/or push-cable 1030 illustrated in FIG. 10 to be moved.

The frame mounting element 1940 may snap onto an inward facing section of the assembled front housing element 1920 and back housing element 1930 and secure about a section of the frame 1010 (FIG. 10). A front housing frame mounting post half 1924 formed on the inward facing section of the front housing element 1920 and a back housing frame mounting post half 1934 formed on the inward facing section of the back housing element 1930 may secure within a hole (not illustrated) formed on the frame of FIG. 10 and hold the camera guide and securing mechanism 1080 against unwanted rotations about the frame (FIG. 10). Additional details of one embodiment of a camera guide and securing mechanism 2080 are shown in FIGS. 20-23 and FIG. 24. The camera guide and securing mechanism 2080 may correspond with corresponding elements 1080.

Figure 20:
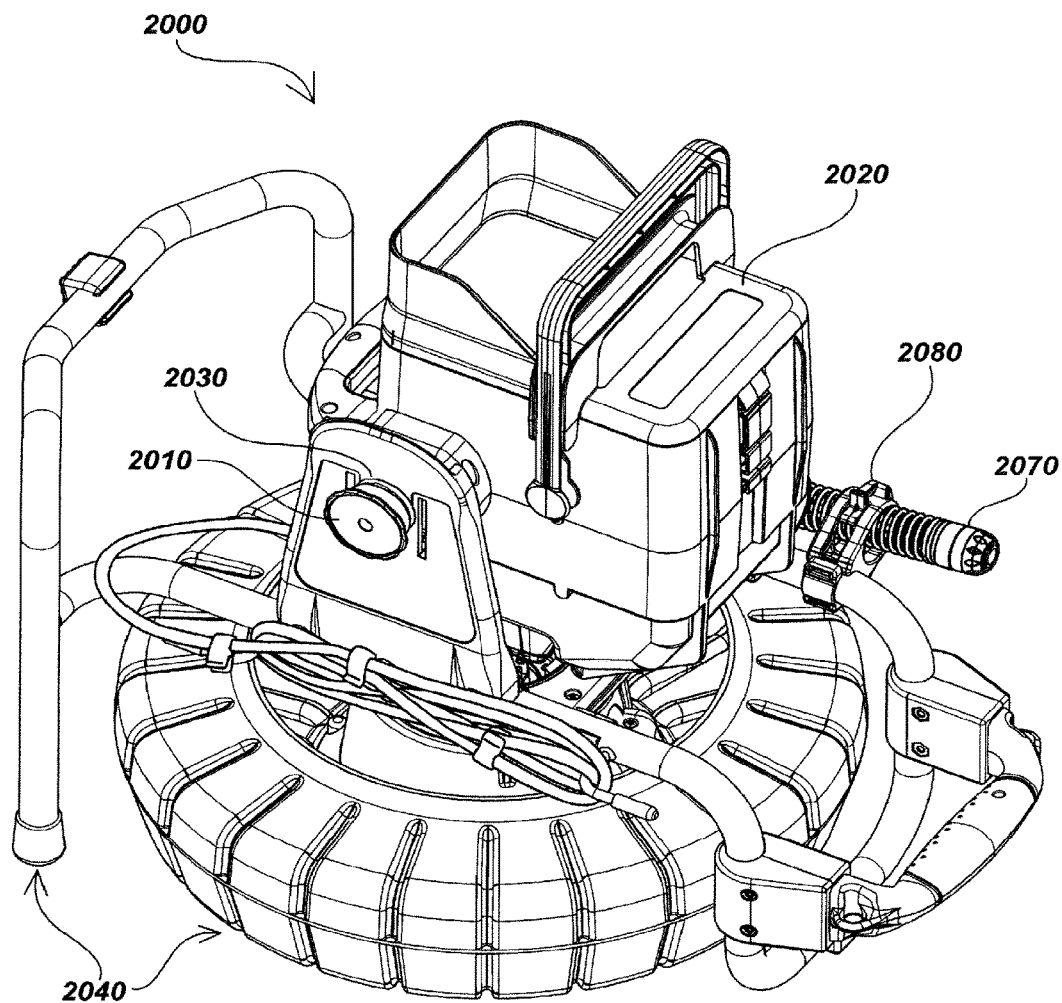
FIG. 20 illustrates an embodiment of a cable storage drum with a moveable CCU docking apparatus with the CCU in an upright position.

Turning to FIG. 20, an embodiment 2000 of a cable storage drum with a moveable CCU docking apparatus, with the CCU in an upright viewing position (assuming the frame and drum assembly 2040 is positioned on the ground or other surface as shown), is shown. This configuration varies from that shown in FIG. 21 which shows the CCU in a horizontal viewing orientation. As shown in FIG. 20, the CCU 2020 may be rotated, such as about a rotational or pivoting axis defined by the latch 2010, which may also include a corresponding latch indicator 2030. Latch indicator 2030 may provide information indicating latch state, such as released (open) or closed state, in various ways, such as audibly, mechanically, visually, etc. An exemplary embodiment is further described with respect to FIG. 23A and FIG. 23B.

Figure 23A:
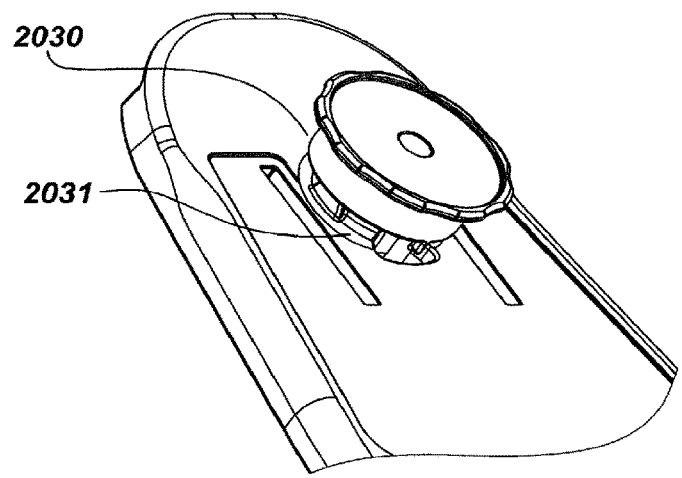
FIGS. 23A and 23B illustrate details of an embodiment of a latch mechanism and latch indicator with visual latch indication.
Figure 23B:
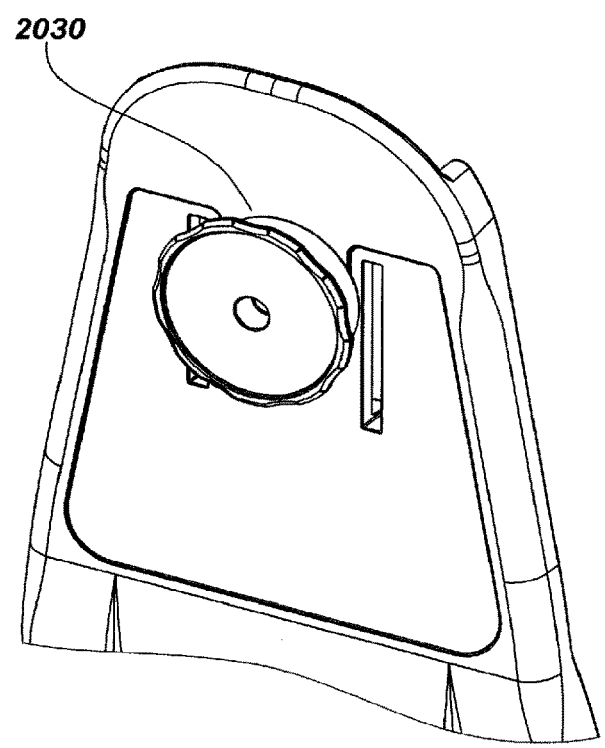
Figure 24:
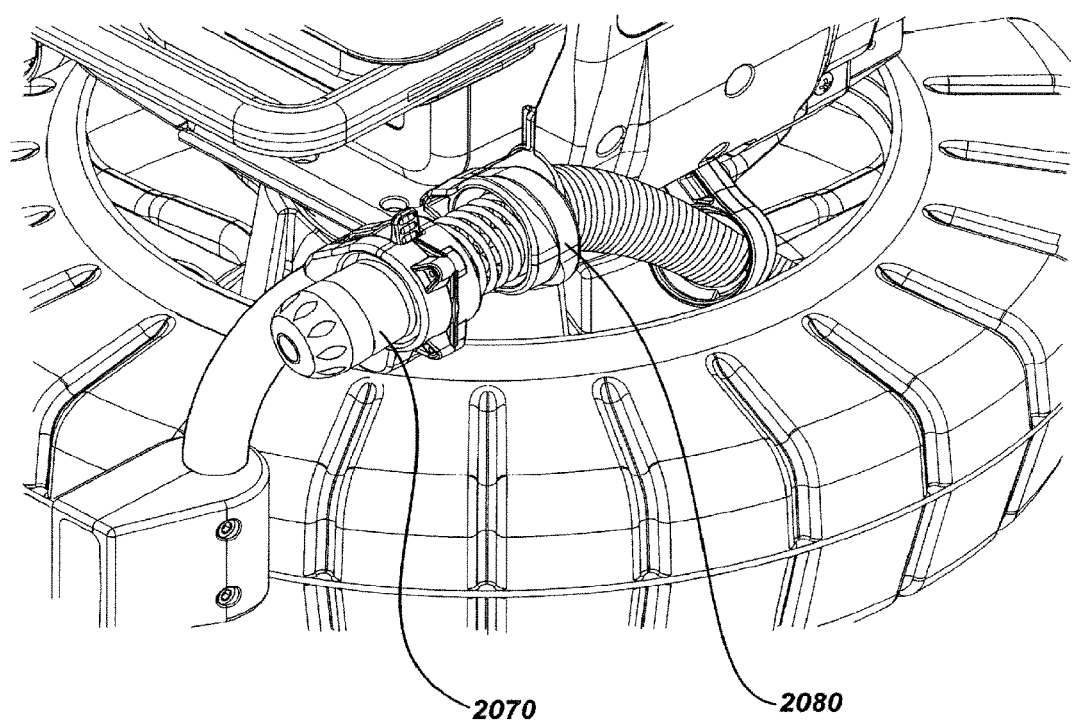
FIG. 24 illustrates details of an embodiment of a camera head with camera guide and securing mechanism.

In an exemplary embodiment, the latch indicator may be a visual indicator that may be colored differently from the frame and/or associated brackets. For example, in embodiments with dark-colored frames or brackets, a bright color, such as bright white, yellow, red, etc. may be used to provide a visual indication to a user that the latch is not secured and that the CCU may come off the corresponding bracket (e.g., by being removed by a user or by falling off, in which case the latch indicator may serve as a warning). In the embodiment shown, latch indicator 2030 includes a colored band, such as a yellow or white band, below the latch knob as shown that only becomes visible when the knob is in an outward or released position relative to the corresponding frame or bracket (e.g., when the knob is moved outward from the frame due to rotation of the knob about the release axis). This is further illustrated in FIGS. 23A and 23B. In FIG. 23A the latch indicator 2030 includes a white or yellow band 2031 inside the knob as shown, that can be seen when the latch knob is outward from the frame. In FIG. 23B, the latch 2030 and corresponding knob are in a locked position next to the frame so that the band 2031 is hidden by the knob so that it cannot be seen.

Figure 21:
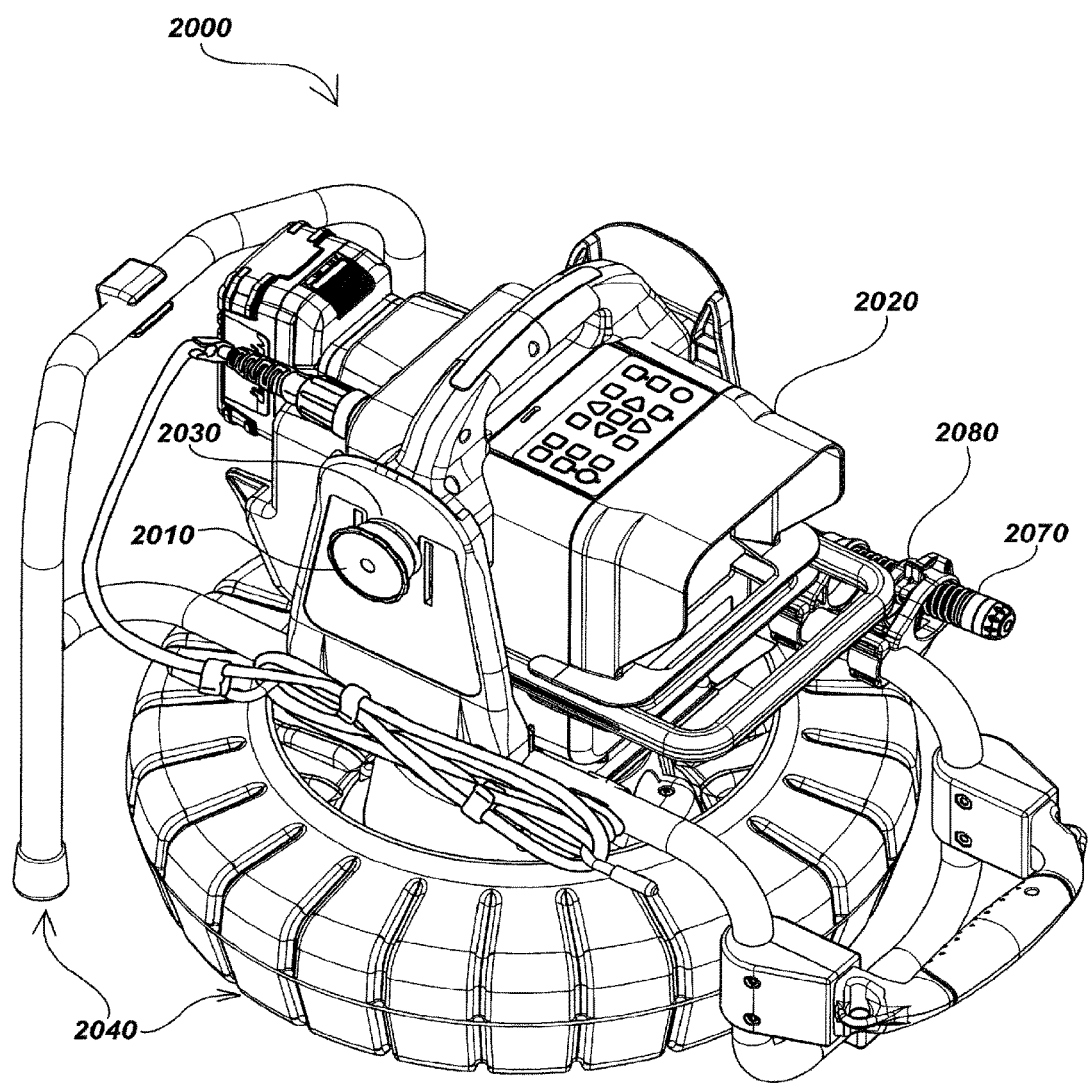
FIG. 21 illustrates an embodiment of a cable storage drum with a moveable CCU docking apparatus with the CCU in a forward-facing position.

FIG. 21 illustrates details of the embodiment 2000 of FIG. 20 with the CCU 2020 in a down or forward-facing position (assuming the frame and drum assembly 2040 are on the ground or other surface as shown in a horizontal orientation). In this orientation, the display of the CCU may be seen by viewing in a horizontal position, while control buttons are accessible on the top of the CCU as shown. The CCU may alternately be positioned in various orientations, such as rotated about an axis defined by the latch 2010 in a rotation position between that shown in FIG. 20 and FIG. 21. In some embodiments, the CCU may be mounted in the opposite orientation relative to the frame and drum so that the display element is facing to the left (rather than to the right as shown).

Figure 22:
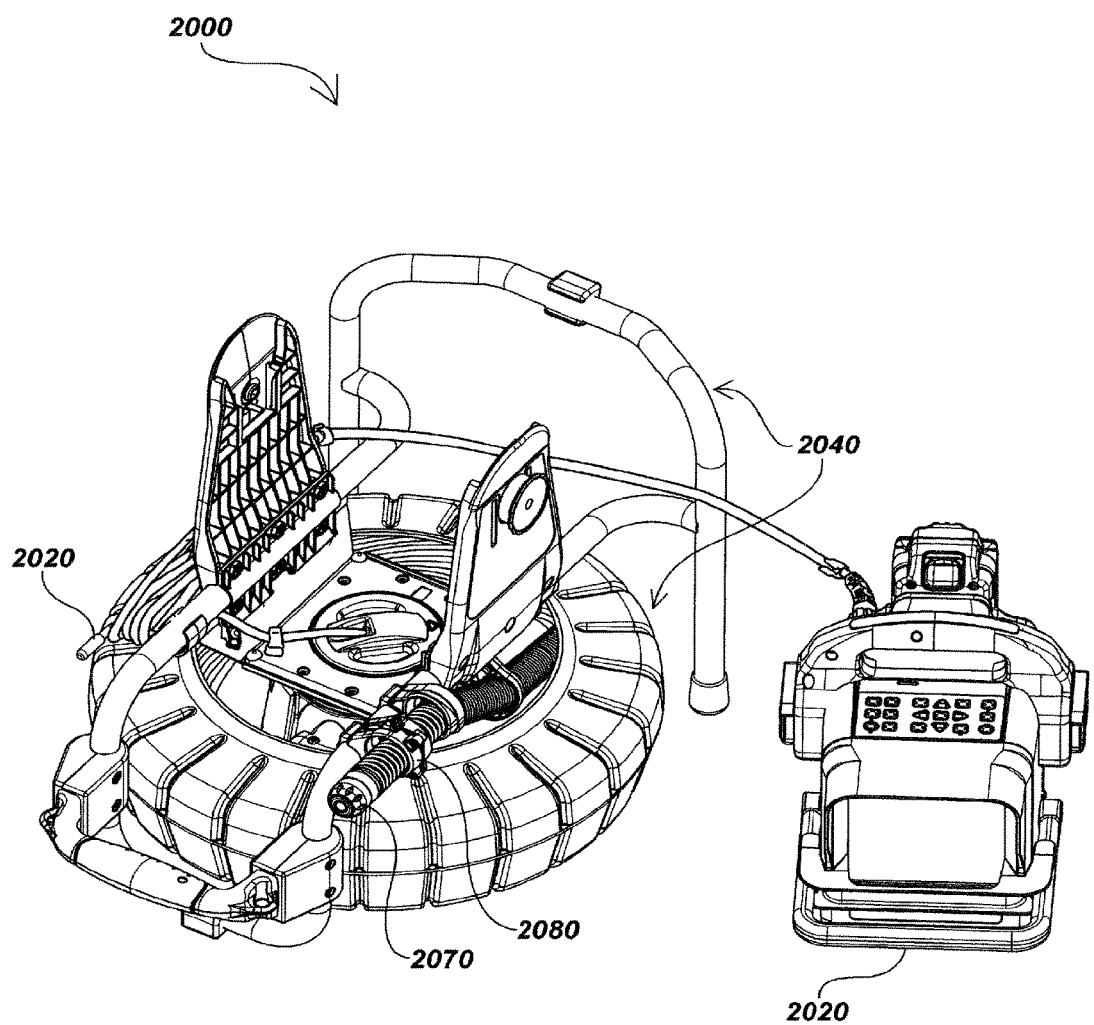
FIG. 22 illustrates an embodiment of a cable storage drum with a moveable CCU docking apparatus with the CCU mechanically disconnected from the drum and frame assembly.

FIG. 22 illustrates details of the embodiment 2000 of FIG. 20 with the CCU 2020 mechanically disconnected from the frame and drum assembly 2040. As shown, the CCU 2020 is still electrically coupled to the cable (stored in the drum) and camera head so that the CCU can be used to operate the camera head and provide displays, store data, and the like.

The present invention is not intended to be limited to the aspects shown herein, but is to be accorded the full scope consistent with the Specification and Drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use various embodiments of the presently claimed invention. Various modifications to these aspects will be readily apparent to those skilled in the art, and the generic principles defined herein may be applied to other aspects without departing from the spirit or scope of the invention. Therefore, the presently claimed invention is not intended to be limited to the aspects and details shown herein, but is to be accorded the widest scope consistent with this appended Claims and their equivalents.

We claim:

1. A video inspection system, comprising:
    a tubular frame;
    a camera head;
    a push-cable;
    a camera control unit (CCU) including a housing, electronics disposed in the housing for controlling operation of the camera head operatively coupled to the electronics, a display disposed in the housing for rendering images or video provided from the camera head, and a non-transitory memory for storing images or video provided from the camera head;
    a donut-shaped cable storage drum enclosing the push-cable when retracted, the cable storage drum coupled to the tubular frame and including a slip-ring for operatively coupling CCU electronic input and output connections to the camera head; and
    a docking apparatus mechanically coupled between the tubular frame and the CCU to allow the CCU to rotate relative to the tubular frame and the cable storage drum, about a rotational axis, responsive to a user action, and allow the CCU to be removably attached or detached, via a user-actuated latching mechanism, to the tubular frame.

2. The system of claim 1, wherein the CCU is partially engaged via a snap-action engagement to the tubular frame.

3. The system of claim 1, wherein the docking apparatus includes a frictional element for restraining rotation of the CCU.

4. The system of claim 1, wherein the latching mechanism includes one or more knobs rotatable on a release axis to release the CCU from attachment to the tubular frame.

5. The system of claim 4, further comprising a latch indicator to indicate a release state or a locked state of the CCU responsive to a user action on the knobs.

6. The system of claim 1, wherein the release state and the locked state are indicated by different color bands.

7. The system of claim 1, wherein the push-cable is disposed at least partially within an interior volume of the cable storage drum and the push-cable is operatively coupled to the CCU via the slip-ring.

8. The system of claim 1, wherein a center of gravity of the CCU is centered at or proximate to a central movable axis of the cable storage drum.

9. The system of claim 1, further comprising one or more handles disposed on at least one of the CCU, the docketing apparatus, or the tubular frame, the handles being designed to be grasped by a user's hand for transportation of the system.

10. The system of claim 1, wherein the CCU is rotatable about a central movable axis of the cable storage drum during transportation of the system.

11. The system of claim 1, wherein the camera head is mechanically coupled to a distal end of the push-cable and the camera head is electronically coupled to the CCU.

12. The system of claim 1, wherein the camera head is a self-leveling camera head.

13. The system of claim 1, further comprising a modular battery apparatus electrically coupled to the CCU to provide operational power for the electronics and the camera head.

14. The system of claim 1, further comprising a counting device configured to determine and measure rotations of the cable storage drum to determine quantity of the push-cable dispensed from the cable storage drum and/or distance travelled by the camera head from the cable storage drum.

15. The system of claim 1, further comprising a wireless communication module disposed in the housing of the CCU to send image or video data from the CCU to a remote communicatively coupled electronic device.

16. A camera control unit (CCU) system, comprising:
a tubular frame;
a camera control unit (CCU) including a housing, electronics disposed in the housing for controlling operation of a camera head operatively coupled to the electronics, a display disposed in the housing for rendering images or video provided from the camera head, and a non-transitory memory for storing images or video provided from the camera head;
a cable storage drum having an interior volume enclosing, at least partially, the push-cable, the cable storage drum is coupled to the tubular frame arranged to remain stationary while allowing the cable storage drum to rotate when dispensing the push-cable therefrom; and
a docking apparatus mechanically coupled between the tubular frame and the CCU to allow the CCU to rotate relative to the tubular frame and the cable storage drum, about a rotational axis, responsive to a user action, and allow the CCU to be removably attached or detached, via a snap and release mechanism, to the tubular frame, wherein the docketing apparatus includes a friction element to retain the CCU in an angled or upright self-supporting position.

17. The system of claim 16, wherein the cable storage drum includes a slip-ring for operatively coupling CCU electronic input and output connections to the camera head.

18. The system of claim 16, wherein a center of mass of the tubular frame and the cable storage drum are below the rotational axis.

19. The system of claim 16, wherein the camera head is mechanically coupled to a distal end of the push-cable and the camera head is electronically coupled to the CCU.

20. The system of claim 1, wherein the snap and release mechanism includes one or more knobs rotatable on a release axis to release the CCU from attachment to the tubular frame.

* * * * *